(12) United States Patent
Engelmayer et al.

(10) Patent No.: US 8,030,272 B2
(45) Date of Patent: *Oct. 4, 2011

(54) LACTOFERRIN COMPOSITIONS AND METHODS OF WOUND TREATMENT

(75) Inventors: Jose Engelmayer, Houston, TX (US); Atul Varadhachary, Houston, TX (US)

(73) Assignee: Agennix Incorporated, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/403,250

(22) Filed: Mar. 12, 2009

(65) Prior Publication Data

US 2009/0253627 A1 Oct. 8, 2009

Related U.S. Application Data

(63) Continuation of application No. 10/663,258, filed on Sep. 16, 2003, now Pat. No. 7,524,814.

(60) Provisional application No. 60/410,981, filed on Sep. 16, 2002.

(51) Int. Cl.
*A61K 38/00* (2006.01)
*A61K 38/40* (2006.01)

(52) U.S. Cl. ............... 514/6; 514/8; 530/350; 530/395; 530/400; 424/9.1; 424/85.1

(58) Field of Classification Search ................ 514/8, 6; 530/350, 395, 400; 424/85.1, 9.1
See application file for complete search history.

(56) References Cited

U.S. PATENT DOCUMENTS

| | | | | |
|---|---|---|---|---|
| 4,783,488 A | 11/1988 | Ogunbiyi et al. | ............ | 514/635 |
| 4,977,137 A | 12/1990 | Nichols | | |
| 5,198,419 A | 3/1993 | Ando et al. | | |
| 5,457,093 A | 10/1995 | Cini et al. | | |
| 5,561,109 A | 10/1996 | Mita et al. | ............ | 514/12 |
| 5,571,691 A | 11/1996 | Conneely et al. | | |
| 5,571,697 A | 11/1996 | Conneely et al. | | |
| 5,571,896 A | 11/1996 | Conneely et al. | | |
| 5,576,299 A | 11/1996 | Ando et al. | ............ | 514/21 |
| 5,766,939 A | 6/1998 | Conneely et al. | | |
| 5,834,424 A | 11/1998 | Valenti et al. | | |
| 5,849,881 A | 12/1998 | Conneely et al. | | |
| 5,955,316 A | 9/1999 | Conneely et al. | | |
| 6,066,469 A * | 5/2000 | Kruzel et al. | ............ | 435/69.1 |
| 6,080,559 A | 6/2000 | Conneely et al. | | |
| 6,100,054 A | 8/2000 | Conneely et al. | | |
| 6,111,081 A | 8/2000 | Conneely et al. | | |
| 6,228,614 B1 | 5/2001 | Conneely et al. | | |
| 6,333,311 B1 | 12/2001 | Nuijens et al. | | |
| 6,399,570 B1 | 6/2002 | Mann | | |
| 6,635,447 B1 | 10/2003 | Conneely et al. | | |
| 7,323,443 B2 | 1/2008 | Varadhachary et al. | ............ | 514/6 |
| 7,524,814 B2 * | 4/2009 | Engelmayer et al. | ............ | 514/6 |
| 2002/0016289 A1 | 2/2002 | Conneely et al. | ............ | 514/8 |
| 2003/0105006 A1 | 6/2003 | Mann | | |
| 2003/0190303 A1 | 10/2003 | Kimber et al. | | |
| 2004/0009895 A1 | 1/2004 | Jung et al. | | |
| 2004/0009896 A1 | 1/2004 | Glynn et al. | | |
| 2004/0082504 A1 | 4/2004 | Varadhachary et al. | | |
| 2004/0142037 A1 | 7/2004 | Engelmayer et al. | ............ | 424/486 |
| 2005/0064546 A1 | 3/2005 | Conneely et al. | | |
| 2005/0075277 A1 | 4/2005 | Varadhachary et al. | | |

FOREIGN PATENT DOCUMENTS

| | | |
|---|---|---|
| JP | 4259467 A | 9/1992 |
| JP | 6192130 A | 7/1994 |
| JP | 6508641 T | 9/1994 |
| JP | 6316530 A | 11/1994 |
| JP | 7196529 A | 8/1995 |
| JP | 07233086 A | 9/1995 |
| JP | 8337526 A | 12/1996 |
| JP | 10310534 A | 11/1998 |
| JP | 10338632 A | 12/1998 |
| JP | 11512740 T | 11/1999 |
| WO | 0143722 A2 | 6/2001 |
| WO | WO-0203910 A2 | 1/2002 |
| WO | WO-02100445 A1 | 12/2002 |
| WO | WO 2004/024180 | 3/2004 |

OTHER PUBLICATIONS

Engelmayer et al. "Talactoferrin Stimulates Wound Healing With Modulation of Inflammation" Journal of Surgical Research, 2008.
Lyons et al. "Talactoferrin alfa, a recombinant human lactoferrin promotes healing of diabetic neuropathic ulcers: a phase 1/2 clinical study" The American Journal of Surgery 193 (2007) 49-54.
Brink, "Lactoferrin: The Bioactive Peptide that Fights Disease," *Life Extension Magazine*, found at http://www.lef.org/LEFCMS/aspx/PringVersionMagic.aspx?CmsID=31812, Oct. 2000.
Legrand et al, "The N-terminal Arg2, Arg3, Arg4 of Human Lactoferrin Interact with Sulphated Molecules but Not with the Receptor Present on Jurkat Human Lymphoblastic T-Cells," Biochem J.vol, 327, pp. 841-846 (1997).
van Berkel et al, "N-terminal Stretch Arg2, Arg3, and Arg5 of Human Lactoferrin is Essential for Binding to Heparin, Bacterial Lipopolysaccharide, Human Lysozyme and DNA," Biochem J. vol. 328, pp. 145-151 (1997).
Yang et al, "Antitumor Activity and Specificity as a Function of Substitutions in the Lipophilic Sector of Helical Lactoferrin-derived Peptide," Journal of Peptide Science 9, 2003, pp. 300-311.
Takayama et al, "The Bovine Lactoferrin Region Responsible for Promoting the Collagen Gel Contractile activity of Human Fibroblasts," Biochemical and Biophysical Research Communications 299 (2002), pp. 813-817.
Yang et al., "Enhanced Antitumor Activity and Selectivity of Lactoferrin-derived peptides," J. Peptide Res. 60, 2002, pp. 187-197.
Takayama et al, "Effects of Lactoferrin on Collagen Gel Contractile Activity and Myosin Light Chain Phosphorylation in Human Fibroblasts," FEBS Letter 508, 2001, pp. 111-116.
Clarke et al, "Evaluation of Bovine Lactoferrin as a Topical Therapy for Chemotherapy-induced Mucositis in the Golden Syrian Hamster," Oral Oncology 35, 1999, pp. 197-202.
Fujihara et al, "Lactoferrin Protects Against UV-B Irradiation-Induced Corneal Epithelial Damage in Rats," Cornea 19(2); 2000, pp. 207-211.
Nakajima et al, "Lactoferrin as a Suppressor of Cell Migration of Gastrointestinal Cell Lines," Journal of Cellular Physiology 170, 1997, pp. 101-105.

(Continued)

*Primary Examiner* — Chih-Min Kam
(74) *Attorney, Agent, or Firm* — Fulbright & Jaworski L.L.P.

(57) ABSTRACT

The present invention relates to lactoferrin compositions and methods of using the compositions to treat wounds. The compositions can be administered alone or in combination with other standard wound healing therapies.

18 Claims, 7 Drawing Sheets

OTHER PUBLICATIONS

Weinberg, Eugene, "The Therapeutic Potential of Lactoferrin," Expert Opinion Investig. Drugs, 12(5), 2003, pp. 841-851.

Cumberbatch et al, "IL-I B-induced Langerhans' cell Migration and TNF-A production in Human Skin: Regulation by Lactoferrin," Clin Exp. Immunol 132, 2003, pp. 352-359.

He et al, "The Inhibition of Mast Cell Activation by Neutrophil Lactoferrin: Uptake by Mast Cells and Interaction with Tryptase, Chymase and Cathepsin G," Biochemical Pharmacology 65, 2003, pp. 1007-1015.

Kimber et al, "Lactoferrin: Influence on Langerhans Cells, Epidermal Cytokines, and Cutaneous Inflammation," Biochem Cell Biol. 80, 2002, pp. 103-107.

Ward et al, "Lactoferrin and Host Defense," Biochem Cell Biol. 80, 2002, pp. 95-102.

Cumberbatch et al, "Regulation of Epidermal Langerhans Cell Migration by Lactoferrin," Immunology 2000, 100, pp. 21-28.

U.S. Appl. No. 10/733,621, Agennix Incorporated.

U.S. appl. No. 10/728,521, Agennix Incorporated.

U.S. Appl. No. 10/728,275, Agennix Incorporated.

U.S. Appl. No. 10/844,865, Agennix Incorporated.

U.S. Appl. No. 10/732,429, Agennix Incorporated.

U.S. Appl. No. 10/862,213, Agennix Incorporated.

Japanese Notification of Reasons for Refusal issued Oct. 9, 2009 during prosecution of Japanese Patent Application No. 2004-536558.

Supplementary European Search Report issued May 8, 2009 during prosecution of European Patent Application No. EP 03 75 2398.

"Contemporary Traumatology," Li Ao, editor-in-chief, People's Medical Publishing House, $1^{st}$ Ed., $1^{st}$ Printing, English language translation of p. 69, paragraphs 4-6; p. 70, paragraphs 2-3; p. 116; and p. 142, last paragraph to p. 143, paragraph 2, Dec. 1996.

De la Torre and Chambers, "Wound Healing, Chronic Wounds," eMedicine Specialties> Plastic Surgery> Wound Healing; eMedicine.medscape.com; Oct. 9, 2008.

Ehrlich and Hunt, "Effects of Cortisone and Vitamin A on Wound Healing," Annals of Surgery,167(3):324-328, 1968.

Engelmayer et al., "Talactoferrin Stimulates Wound Healing with Modulation of Inflammation," Journal of Surgical Research, 149(2):278-286, 2008.

English language translation of Notice of Reexamination issued Jun. 9, 2010 during the prosecution of Chinese Patent Application No. 03825068.3.

Gabriel et al., "Wound Healing, Growth Factors," eMedicine Specialties > Clinical Procedures > Soft Tissue Procedures; eMedicine.medscope.com; Feb. 17, 2006.

Mercandetti et al., "Wound Healing, Healing and Repair," eMedicine Specialties >Plastic Surgery > Wound Healing; emedicine.medscape.com; Mar. 27, 2008.

Mulvaney and Harrington, "Cutaneous Trauma and its Treatment," Military Dermatology; Chapter 7, pp. 143-156, 1994.

Takayama et al., "Low Density Lipoprotein Receptor-related Protein (LRP) is Required for Lactoferrin-enhanced Collagen Gel Contractile Activity of Human Fibroblasts," The Journal of Biological Chemistry, 278(24):22112-22118, 2003.

Definition of proctitis in the medical dictionary, (2008).

* cited by examiner

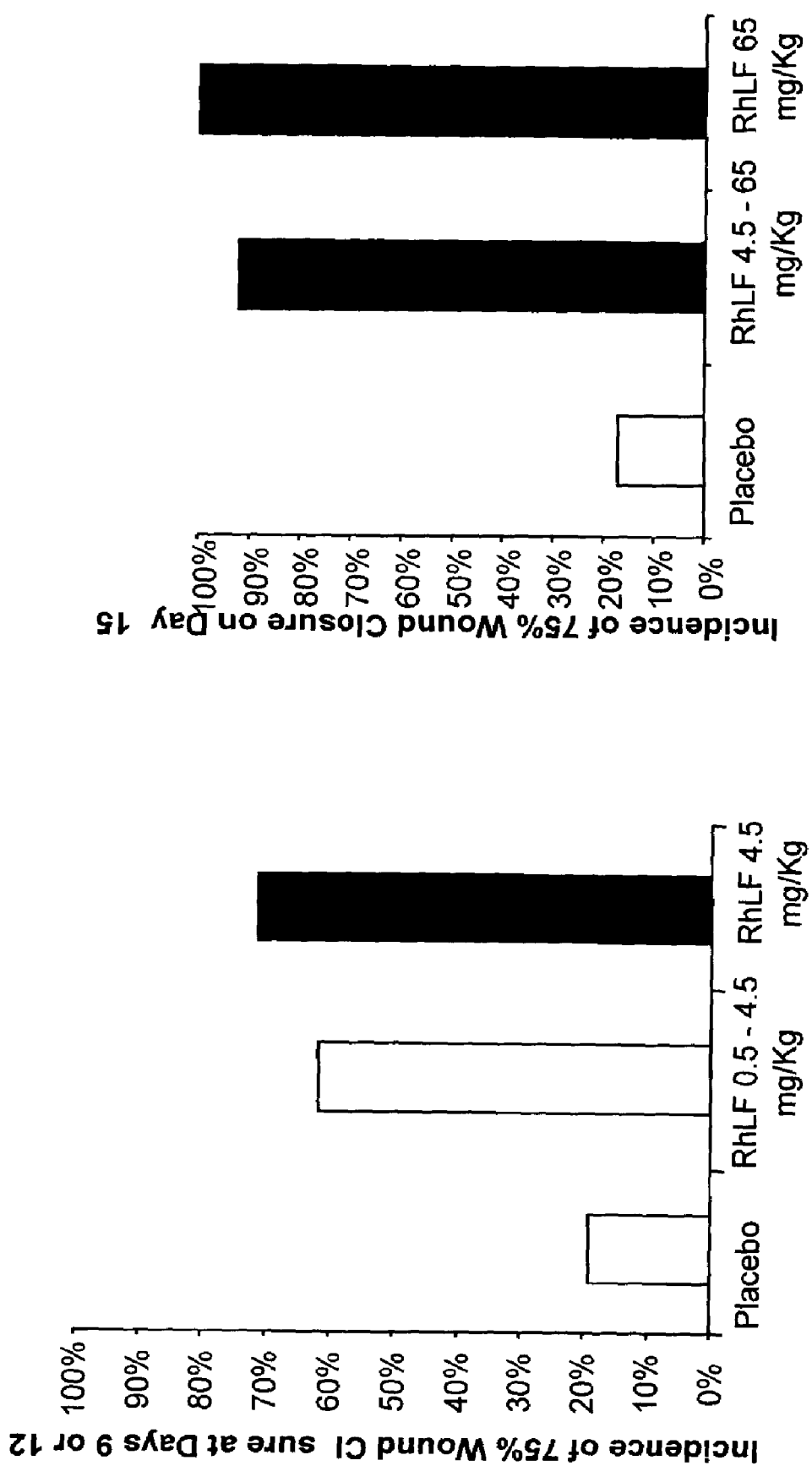

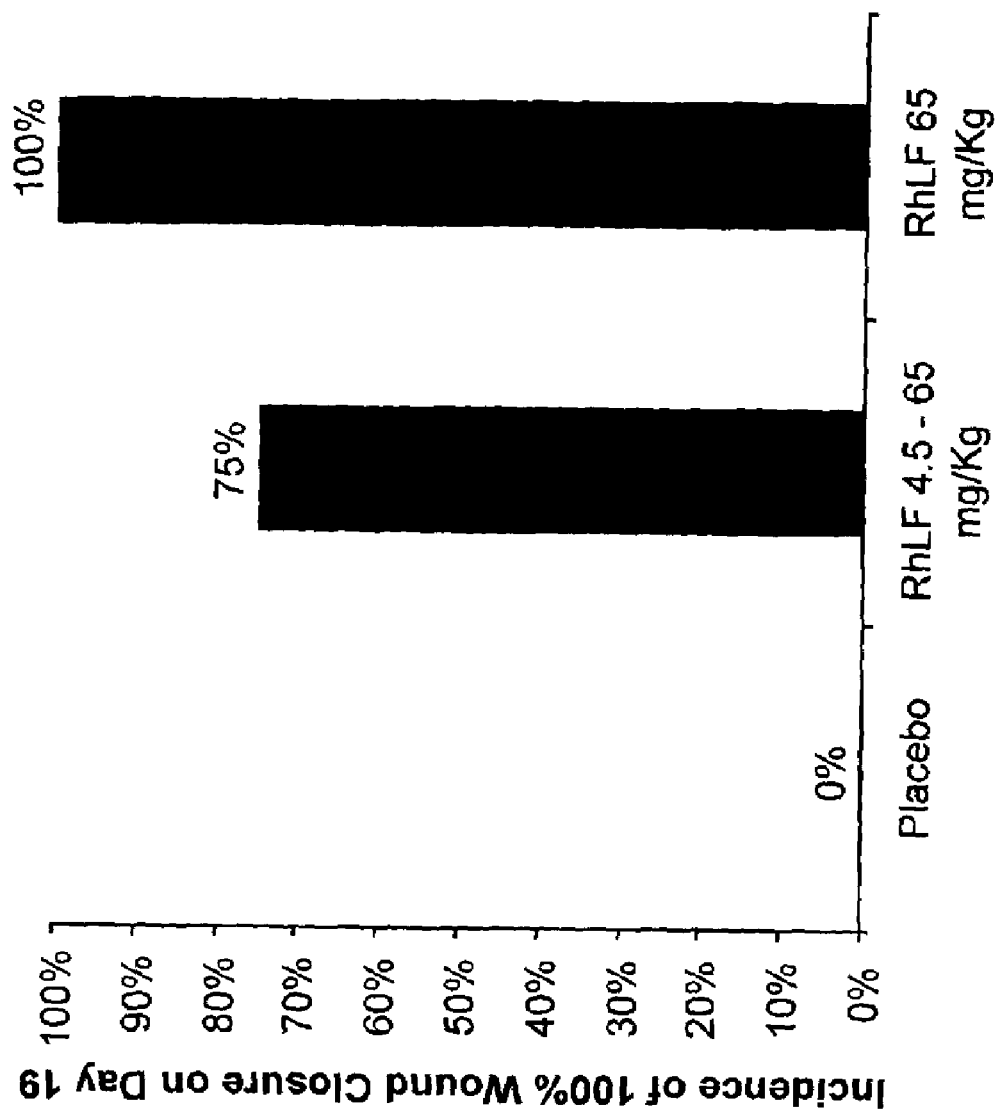

LACTOFERRIN COMPOSITIONS AND METHODS OF WOUND TREATMENT

CROSS-REFERENCE TO RELATED APPLICATIONS

This application is a continuation of U.S. patent application Ser. No. 10/663,258 filed 16 Sep. 2003, now U.S. Pat. No. 7,524,814, which claims the benefit of Provisional Application No. 60/410,981 filed on Sep. 16, 2002 which is incorporated herein by reference.

TECHNICAL FIELD

The present invention relates to lactoferrin compositions and methods of using the compositions to treat wounds. The compositions can be administered alone or in combination with other standard wound healing therapies. Yet further, the compositions can also comprise a metal chelator.

BACKGROUND OF THE INVENTION

Relatively few biotechnology products have been developed for treating wounds, such as partial-thickness burns. Most of the efforts have been directed towards chronic wounds, which do require a proper level of cellular growth factors for healing. The most conventional option of chronic ulcer treatment involves sharp debridement to remove all non-viable tissue, a non-weight-bearing regimen, moist saline dressings changed twice daily at which times the skin around the ulcer are cleansed with mild soap and water. Current advanced treatment for chronic ulcers include growth factors, skin replacement therapy, enzymatic and mechanical debridement to clean ischemic tissue, moist wound dressings, non-antibiotic cleansers, antibiotics (Edmonds et al., 2000, Lipsky and Berendt 2000, Moulin et al., 1998, Mandracchia et al., 2001). However, current therapy for chronic wounds is not completely effective. In fact, Regranex™ gel or Becaplermin (recombinant-human platelet-derived growth factor-BB), the only biological product in the market for chronic wounds (diabetic neuropathic ulcers) has shown only 9-23% improvement over placebo and 4-22% improvement over good ulcer care alone (Mandracchia et al., 2001, Edmonds et al., 2000, Wieman 1998). Thus, an effective treatment for wounds, chronic and/or acute, is needed.

Lactoferrin is an immunomodulatory human protein expressed throughout the body and found in highest concentrations in milk and colostrums. Recombinant human lactoferrin (RhLF) is a recombinant glycoprotein produced in *Aspergillus niger* (*A. niger*), a filamentous fungi. RhLF is structurally identical in all material respects to native lactoferrin and has a wide array of functions related to host defense mechanisms. For example, lactoferrin has been reported to activate natural killer (NK) cells, induce colony stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity.

Recombinant human lactoferrin has previously been described as being purified after expression in a variety of prokaryotic and eukaryotic organisms including *aspergillus* (U.S. Pat. No. 6,080,559), cattle (U.S. Pat. No. 5,919,913), rice, corn, *Sacharomcyes* (U.S. Pat. No. 6,228,614) and *Pichia pastoris* (U.S. Pat. Nos. 6,455,687, 6,277,817, 6,066, 469). Also described are expression systems for the expression of full-length human lactoferrins (e.g., U.S. Pat. No. 6,100,054). In all cases, part of the teaching is expression of the full length cDNA and purification of the intact protein whose N-terminal, after processing of the leader peptide, is the amino acid glycine. Nuijens et al. (U.S. Pat. No. 6,333,311) separately describe variants of human lactoferrin but their focus is limited to deletion or substitution of arginine residues found in the N-terminal domain of lactoferrin.

EDTA (ethylenediaminetetraacetic acid) is a synthetic compound which has well known metal-binding characteristics. EDTA is most commonly used for chelation therapy, a treatment that involves repeated intravenous administration of EDTA to pull toxins from the bloodstream. EDTA administration is the medically accepted treatment for poisoning by heavy metals such as lead, mercury, arsenic and thallium and has been approved by the Food and Drug Administration (FDA) for this use.

EDTA has also been proposed as a treatment for heart disease. Proponents of chelation therapy for heart disease claim that EDTA, in combination with oral vitamins and minerals, helps dissolve plaques and mineral deposits associated with atherosclerosis. Although many Americans with heart disease have turned to EDTA chelation therapy to improve their condition, the FDA has not approved this therapy as an alternative treatment for heart disease. It is thought that EDTA chelation may help strengthen the immune system by sequestering impurities from the bloodstream.

The present invention is the first to develop a suitable delivery system to deliver lactoferrin to treat acute and/or chronic ulcers or other types of wounds, such as burns. Yet further, the present invention is the first to use lactoferrin in combination with a metal chelator to treat acute and/or chronic wounds.

BRIEF SUMMARY OF THE INVENTION

The present invention is directed to a composition comprising lactoferrin or N-terminal lactoferrin variant in which at least the N-terminal glycine residue is truncated or substituted. The composition can be used as a treatment for wound healing. The method of treatment involves the administration of the lactoferrin composition, which may be applied topically, orally or parenterally. The lactoferrin composition can also be administered in combination with standard wound healing therapies.

An embodiment of the present invention comprises a lactoferrin composition having an N-terminal lactoferrin variant. More specifically, the lactoferrin is recombinant lactoferrin variant. Such N-terminal lactoferrin variants includes variants that at least lack the N-terminal glycine residue or contain a substitution at the N-terminal glycine residue. The substitution can comprise substituting a natural or artificial amino acid residue for the N-terminal glycine residue. For example, the substitution can comprise substituting a positive amino acid residue or a negative amino acid residue for the N-terminal glycine residue or substituting a neutral amino acid residue other than glycine for the N-terminal glycine residue. Other N-terminal lactoferrin variants include lactoferrin lacking one or more N-terminal residues or having one or more substitutions in the N-terminal.

In specific embodiments, the N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

An embodiment of the present invention is a pharmaceutical composition comprising a therapeutically effective amount of a lactoferrin composition and a pharmaceutically acceptable polymer having a viscosity in the range of about 1 to about 12,000,000 cP at room temperature, wherein the amount of lactoferrin is sufficient to provide an improvement in the wound. The lactoferrin is mammalian lactoferrin, such as human or bovine. More specifically, the lactoferrin is recombinant lactoferrin. Still further, the lactoferrin composition comprises a variant thereof in that at least the N-terminal glycine is truncated and/or substituted. The N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

In specific embodiments, the polymer is selected from the group consisting of vinyl polymer (i.e., polyacrylic acid, polymethacrylic acid, polyvinyl pyrrolidone and polyvinyl alcohol), polysaccharide polymer (i.e., cellulose, cellulose derivatives, glycosaminoglycans, agar, pectin, alginic acid, dextran, starch, and chitosan), glycosaminoglycan polymer (i.e., hyaluronic acid, chondroitin, chondroitin-4-sulfate, chondroitin-6-sulfate, dermatan sulfate, keratan sulfate, heparin sulfate and heparin), protein polymer (i.e., collagen, gelatin and fibronectin), polyoxyethylene-polyoxypropylene polymer (i.e., polyoxyethylene-polyoxypropylene block copolymer) and acrylamide polymer (i.e., polyacrylamide or polymethacrylamide). Preferably, the polyoxyethylene-polyoxypropylene block copolymer is F88 or F127.

In further embodiments, the lactoferrin (lactoferrin or N-terminal lactoferrin variant in which at least the N-terminal glycine residue is truncated or substituted) concentration of the pharmaceutical composition is within the range of about 0.0001% (w/w) to about 30% (w/w). More particularly, the polymer concentration is about 0.5% (w/w) to about 3.0% (w/w) and the polymer has an average molecular weight of about 500 to about 13,000,000.

A preferred embodiment is a pharmaceutical composition comprising an amount of recombinant human lactoferrin (rhLF lactoferrin or an N-terminal lactoferrin variant thereof such that at least the N-terminal glycine residue is truncated or substituted) that is sufficient to provide an improvement in a wound, and a polymer, wherein the polymer is selected from the group consisting of a vinyl polymer, polysaccharide polymer, glycosaminoglycan polymer, protein polymer, polyoxyethylene-polyoxypropylene polymer, and acrylamide polymer, wherein the composition is an aqueous gel having a viscosity in the range of about 1 to about 12,000,000 cP at room temperature. The polymer concentration is about 0.5% (w/w) to about 3.0% (w/w) and the polymer has a molecular weight of about 500 to about 13,000,000.

Another preferred embodiment is a pharmaceutical composition comprising an amount of a lactoferrin composition that is sufficient to provide an improvement in a wound and a pharmaceutically acceptable polymer selected from the group consisting of a vinyl polymer, polysaccharide polymer, glycosaminoglycan polymer, protein polymer, polyoxyethylene-polyoxypropylene polymer, and acrylamide polymer having a concentration in the range of about 0.5% (w/w) to about 3.0% (w/w) and having a molecular weight in the range of about 500 to about 13,000,000, wherein the composition is an aqueous gel having a viscosity in the range of about 1 to about 12,000,000 cP at room temperature.

Another embodiment of the present invention is a method of treating a wound comprising the step of administering to a subject a lactoferrin composition in an amount sufficient to provide an improvement in the wound. The lactoferrin composition is dispersed in a pharmaceutically acceptable carrier. In further embodiments, the lactoferrin composition is administered in combination with other standard wound healing therapies. The lactoferrin composition can be administered for at least one week, six weeks, 12 weeks, 36 weeks, etc. or any range in between.

In further embodiments, a metal chelator dispersed in a pharmaceutically acceptable carrier may also be administered with the lactoferrin composition. Preferred metal chelator include, but are not limited to ethylenediaminetetraacetic acid (EDTA) or [ethylenebis(oxyethylenenitrilo)]tetraacetic acid (EGTA). More preferably, the metal chelator is EDTA.

Exemplary wounds that can be treated include, but are not limited to skin wounds, bone wounds, internal wounds gastrointestinal wounds, oral wounds, ophthalmic wounds, surgical wounds, or any combination thereof. A skin wound can be a full-thickness skin wound or a partial-thickness skin wound. In specific embodiments, the wound is further defined as a chronic wound, for example, but not limited to diabetic ulcer, venous stasis ulcer, pressure ulcer, and infected wound. Still further, the wound is further defined as an acute wound. Exemplary acute wounds include, but are not limited to first degree burn, partial-thickness burn, full-thickness burn, laceration, bullet wound, and infected wound.

In further embodiments, the lactoferrin is administered topically, orally or parenterally. Still further, an antacid may also be administered in conjunction with said lactoferrin composition.

In specific embodiments, the amount of the lactoferrin composition (lactoferrin or N-terminal lactoferrin variant such that at least the N-terminal glycine residue is truncated or substituted) that is administered is about 0.0001 µg to about 100 g per day. The amount of the EDTA that is administered is about 1 ng to about 1 g per day.

In further embodiments, the lactoferrin composition is a topical gel, a solution, capsule or a tablet having a lactoferrin concentration of about 0.0001% to about 30%. Topical gel is composed from a polymer selected from the group of consisting of a vinyl polymer, polysaccharide polymer, glycosaminoglycan polymer, protein polymer, polyoxyethylene-polyoxypropylene polymer, and acrylamide polymer. The polymer concentration is about 0.5% (w/w) to about 3.0% (w/w) and the polymer has a molecular weight of about 50,000 to about 13,000,000.

Another embodiment is a method of treating a wound comprising the step of supplementing the local immune system in a subject by administering topically the amount of lactoferrin in the vicinity of the wound. The lactoferrin results in the killing of bacteria infecting the wound.

A further embodiment is a method of enhancing the local immune system in a subject suffering from a wound comprising the step of administering topically to the subject a lactoferrin composition. Lactoferrin results in the killing of bacteria infecting the wound. Lactoferrin stimulates the production of a cytokine or a chemokine. Exemplary cytokines that can be stimulated by lactoferrin include, but are not limited to interleukin-18 (IL-18), interleukin-12 (IL-12), granulocyte/macrophage colony-stimulating factor (GM-CSF), and gamma interferon (IFN-γ). Exemplary chemokines include, but are not limited to macrophage inflammatory protein 3 alpha (MIP-3α), macrophage inflammatory protein 1 alpha (MIP-1α), or macrophage inflammatory protein beta (MIP-1β).

The lactoferrin composition of the present invention can also result in inhibition of a cytokine or chemokine. The cytokine is selected from the group consisting of interleukin-2 (IL-2), interleukin-4 (IL-4), interleukin-5 (IL-5), interleukin-10 (IL-10), and tumor necrosis factor alpha (TNF-α).

Still further, the lactoferrin composition can also inhibit the production of matrix metalloproteinases (MMPs).

Still further, interleukin-18 or granulocyte/macrophage colony-stimulating factor stimulates the production or activity of immune cells. The immune cells are selected from the group consisting of T lymphocytes, natural killer cells, macrophages, dendritic cells, and polymorphonuclear cells. More specifically, the polymorphonuclear cells are neutrophils and the T lymphocytes are selected from the group consisting of CD4+, CD8+ and CD3+ T cells.

In a further embodiment, interleukin-18 or granulocyte/macrophage colony-stimulating factor stimulates the production or activity of cells involved in wound repair. The cells involved in wound repair are selected from the group consisting of keratinocytes, endothelial cells, fibroblasts, dendritic cells and myofibroblasts. The inhibition of TNF-alpha further inhibits the migration and maturation of dendritic cells. The dendritic cells are Langerhans cells.

Another embodiment is a method of treating a wound comprising the step of supplementing the systemic immune system in a subject by increasing the amount lactoferrin in the systemic circulation by administering the lactoferrin composition via a parenteral route that is selected from the group consisting of intramuscular, intravenous, intraperitoneal, intraoccular, intraarticular, and a surgical field.

A further embodiment is a method of enhancing the systemic immune system of a subject suffering from a wound comprising the step of parenterally administering to the subject a lactoferrin composition.

Another embodiment is a method of treating a wound comprising the step of supplementing the mucosal immune system in a subject by increasing the amount of lactoferrin in the gastrointestinal tract of the subject by administering orally a lactoferrin composition.

Still further, another embodiment is a method of enhancing the mucosal immune system in a subject suffering from a wound comprising orally administering to the subject a lactoferrin composition.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

In FIG. 2A, * refers to significant compared to buffer ($p<0.05$), ** refers to very significant compared to buffer ($p<0.01$) and # refers to significant compared to CGS-21680 ($p<0.05$). In FIG. 2B, * refers to significant compared to buffer ($p<0.05$), ' refers to significant compared to rhPDGF [Regranex™] ($p<0.05$), ** very significant compared to buffer ($p<0.01$), and "refers to very significant compared to rhPDGF [Regranex™] ($p<0.01$).

FIG. 4A, FIG. 4B and FIG. 4C show the effect of oral rhLF on the incidence of 75% wound closure in healthy (FIG. 4A) and diabetic (FIG. 4B) mice, and on the incidence of 100% wound closure in diabetic mice (FIG. 4C).

DETAILED DESCRIPTION OF THE INVENTION

Figure 1:
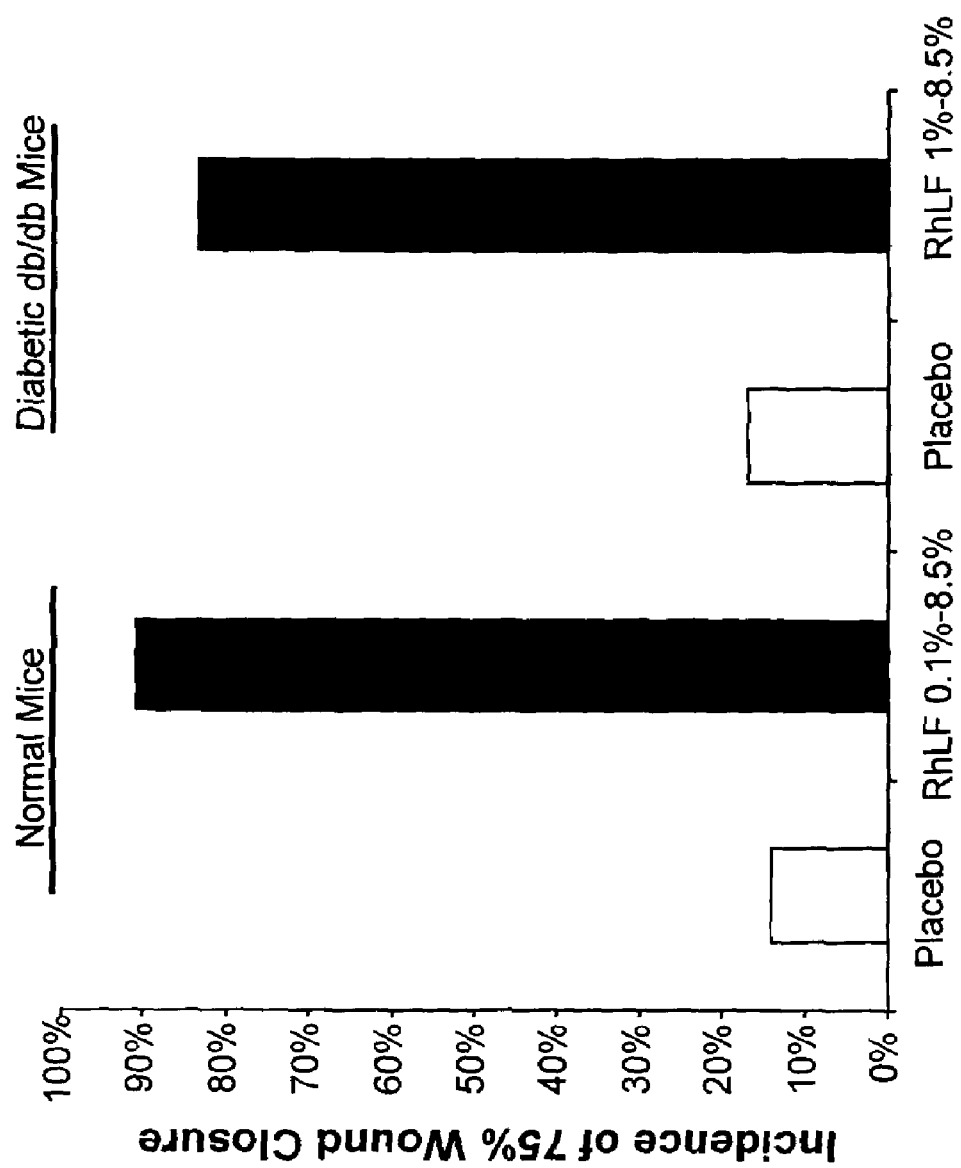
FIG. 1 shows the incidence of 75% wound closure with and without administration of recombinant human lactoferrin carbopol gels in healthy and diabetic mice.

It is readily apparent to one skilled in the art that various embodiments and modifications can be made to the invention disclosed in this Application without departing from the scope and spirit of the invention.

A. DEFINITIONS

As used herein, the use of the word "a" or "an" when used in conjunction with the term "comprising" in the claims and/or the specification may mean "one," but it is also consistent with the meaning of "one or more," "at least one," and "one or more than one."

The term "acute wound" as used herein refers to a wound that heals in a short amount of time. Examples of acute wounds include, but are not limited to partial-thickness burn, laceration, bullet wound or infected wound.

The term "chronic wound" as used herein refers to wounds that take a long time to heal or that do not heal without external intervention. Yet further, as used herein, a "chronic wound", also referred to as "chronic ulcer" can be broadly classified into three major types: diabetic ulcers, venous stasis ulcers, decubitus or pressure ulcers. Still further, a chronic wound can also include infected wounds that take a long time to heal.

The term "cytokine" as used herein refers to proteins that are made by cells that affect the behavior of other cells, for example stimulate or inhibit cell proliferation. For example, cytokines that are made by lymphocytes are often called lymphokines or interleukins. One of skill in the art realizes that the term cytokine is a generic term used in the literature to refer to proteins that are made by cells that can effect the behavior of other cells.

The term "chemokine" as used herein refers to small cytokines that are involved in the migration and activation of cells, for example phagocytic cells and lymphocytes. One of skill in the art realizes that chemokines play a central role in inflammatory and immune response processes.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "lactoferrin composition" as used herein refers to a composition having lactoferrin or a part thereof, wherein at least the N-terminal glycine residue is truncated or substituted.

The term "metal chelator" as used herein refers to a compound which binds metal. Metal chelators that can be used in the present invention include the divalent metal chelators, for example, ethylenediaminetetraacetic acid (EDTA), [ethylenebis (oxyethylenenitrilo)]tetraacetic acid (EGTA), 1,2-bis (2-aminophenoxy)ethane-N,N,N',N'-tetraacetic acid (BAPTA), hydroxyethlene triamine diacetic acid, (HEDTA) or salts thereof.

The term "N-terminal lactoferrin variant" as used herein refers to lactoferrin wherein at least the N-terminal glycine has been truncated and/or substituted. N-terminal lactoferrin variants also include, but are not limited to deletion and/or substitution of one or more N-terminal amino acid residues, for example 1, 2, 3, 4, 5, 6, 7, 8, 9, 10, 11, 12, 13, 14, 15, or 16 N-terminal amino acid residues, etc. Thus, N-terminal lactoferrin variants comprise at least deletions or truncations and/or substitutions of 1 to 16 N-terminal amino acid residues. The deletion and/or substitution of at least the N-terminal glycine of lactoferrin mediates the same biological effects as full-length lactoferrin and/or may enhance lactoferrin's biological activity, for example by stimulating the production of various cytokines (i.e., IL-18, MIP-3α, GM-CSF or IFN-γ), by inhibiting various cytokines, (i.e., IL-2, IL-4, IL-5, IL-10, and TNF-α), and/or by stimulating or promoting wound healing.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intraocular, or intraarticular administration. Yet further, parenteral administration also includes administration into a surgical field.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "pharmaceutical composition" as used herein refers to a lactoferrin composition that this dispersed in a pharmaceutically acceptable carrier. The lactoferrin composition can comprise lactoferrin or an N-terminal lactoferrin variant in which at least the N-terminal glycine amino acid residue is truncated or substituted.

The term "oral administration" as used herein includes, but is not limited to, oral, buccal, enteral or intragastric administration.

The term "subject" as used herein, is taken to mean any mammalian subject to which a human lactoferrin composition is orally administered according to the methods described herein. In a specific embodiment, the methods of the present invention are employed to treat a human subject. Another embodiment includes treating a human subject suffering from a wound.

The term "therapeutically effective amount" as used herein refers to an amount that results in an improvement or remediation of the symptoms of the disease or condition.

The term "topical administration" as used herein includes, but is not limited to topical, dermal (e.g., trans-dermal or intra-dermal), epidermal, or subcutaneous.

The term "treating" and "treatment" as used herein refers to administering to a subject a therapeutically effective amount of a recombinant human lactoferrin composition so that the subject has an improvement in the disease. The improvement is any improvement or remediation of the symptoms. The improvement is an observable or measurable improvement. Thus, one of skill in the art realizes that a treatment may improve the disease condition, but may not be a complete cure for the disease.

The term "wound" as used herein refers to any injury, such as an ulcer, as a result of disease or disorder, or as a result of an accident, incident, or surgical procedure. Wound can be further defined as acute and/or chronic.

B. LACTOFERRIN

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is produced recombinantly using genetic engineering techniques well known and used in the art, such as recombinant expression or direct production in genetically altered animals, plants or eukaryotes, or chemical synthesis. See, i.e., U.S. Pat. Nos. 5,571,896; 5,571,697 and 5,571,691, which are herein incorporated by reference.

In certain aspects, the present invention provides lactoferrin variants having enhanced biological activities of natural LF and or rLF, e.g., the ability to stimulate and/or inhibit cytokines or chemokines. In particular, the invention provides variants of lactoferrin from which at least the N-terminal glycine residue has been substituted and/or truncated. The N-terminal lactoferrin variants may occur naturally or may be modified by the substitution or deletion of one or more amino acids.

The deletional variants can be produced by proteolysis of lactoferrin and/or expression of a polynucleotide encoding a truncated lactoferrin as described in U.S. Pat. No. 6,333,311, which is incorporated herein by reference.

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5; cysteine (−1.0); methionine (−1.3); valine (−1.5); leucine (−1.8); isoleucine (−1.8); tyrosine (−2.3); phenylalanine (−2.5); tryptophan (−3.4).

Still further, it is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Thus, in the present invention, substitutional variants or replacement can be produced using standard mutagenesis techniques, for example, site-directed mutagenesis as disclosed in U.S. Pat. Nos. 5,220,007; 5,284,760; 5,354,670; 5,366,878; 5,389,514; 5,635,377; 5,789,166, and 6,333,311, which are incorporated herein by reference. It is envisioned that at least the N-terminal glycine amino acid residue can be replaced or substituted with any of the twenty natural occurring amino acids, for example a positively charged amino acid (arginine, lysine, or histidine), a neutral amino acid (alanine, asparagine, cysteine, glutamine, glycine, isoleucine, leucine, methionine, phenylaline, proline, serine, threonine, tryptophan, tyrosine, valine) and/or a negatively charged amino acid (aspartic acid or glutamic acid). Still further, it is contemplated that any amino acid residue within the range of N1 to N16 can be replaced or substituted. It is envisioned that at least up to 16 of the N-terminal amino acids residues can be replaced or substituted as long as the protein retains it biological and/or functional activity, which is stimulating the production of various cytokines, such as IL-18, MIP-3α, GM-CSF or IFN-γ, or inhibiting production of various cytokines, such as IL-2, IL-4, IL-5, IL-10, and TNF-α, or promoting wound healing. Thus, the N-terminal lactoferrin variants of the present invention are considered functional equivalents of lactoferrin.

In terms of functional equivalents, it is well understood by the skilled artisan that, inherent in the definition of a "biologically functional equivalent" protein is the concept that there is a limit to the number of changes that may be made within a defined portion of the molecule while retaining a molecule with an acceptable level of equivalent biological activity and/or enhancing the biological activity of the lactoferrin molecule. Biologically functional equivalents are thus defined herein as those proteins in which selected amino acids (or codons) may be substituted. Functional activity is defined as the ability of lactoferrin to stimulate or inhibit various cytokines or chemokines and/or stimulate or promote wound healing.

Still further, the N-terminal amino acid residues can be substituted with a modified and/or unusual amino acids. A table of exemplary, but not limiting, modified and/or unusual amino acids is provided herein below.

TABLE 5

Modified and/or Unusual Amino Acids

| Abbr. | Amino Acid |
|---|---|
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

The presence and the relative proportion of an N-terminal lactoferrin variants (deletions and/or subsititutions) in a preparation of lactoferrin (lactoferrin composition) may be done by determination of the N-terminal amino acid sequence by the process of Edman degradation using standard methods. A relative proportion of N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

In this method, the protein is reacted with phenylisothiocyanate (PITC), which reacts with the amino acid residue at the amino terminus under basic conditions to form a phenylthiocarbamyl derivative (PTC-protein). Trifluoroacetic acid then cleaves off the first amino acid as its anilinothialinone derivative (ATZ-amino acid) and leaves the new amino terminus for the next degradation cycle.

The percentage of N-terminal lactoferrin variant may also be done more precisely by using a Dansylation reaction. Briefly, protein is dansylated using Dansyl chloride reacted with the protein in alkaline conditions (pH 10). Following the Dansylation, the reaction mixtures are dried to pellets, then completely hydrolyzed in 6N HCl. The proportion of N-terminal amino acids are identified by RP HPLC using an in-line fluorometer in comparison with standards made up of known dansylated amino acids.

C. PHARMACEUTICAL COMPOSITIONS

The present invention is drawn to a composition comprising a lactoferrin composition that is dispersed in a pharmaceutical carrier. The lactoferrin that is contained in the composition of the present invention comprises lactoferrin or an N-terminal lactoferrin variant in which at least the N–1 terminal glycine residue is truncated or substituted. More specifically, the N-terminal lactoferrin variant comprises at least 1% of the composition, at least 5% of the composition, at least 10% of the composition, at least 25% of the composition, at least 50% of the composition or any range in between.

Yet further, the composition comprises lactoferrin in combination with a metal chelator dispersed in a pharmaceutical carrier. Thus, the present invention is drawn to a lactoferrin composition with or without a metal chelator that is dispersed in a pharmaceutical carrier. One of skill in the art understands that both compositions (e.g., lactoferrin alone or lactoferrin in combination with a metal chelator) are within the scope of the present invention and can be used interchangeably depending upon the type of response that is desired. It is envisioned that the addition of a metal chelator to the lactoferrin composition enhances the sequestering of metal ions and thus strengthens the immune system or enhances the effect of lactoferrin.

Metal chelators that can be used in combination with lactoferrin, include the divalent metal chelators, for example, ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or any salts thereof. More preferably, EDTA is used in combination with lactoferrin.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach or in the open wound environment. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. Yet further, it is envisioned that divalent metal chelators, for example EDTA, can also be used to stabilize the composition of the present invention. More preferably, for an orally administered composition, the stabilizer can also include antagonists to the secretion of stomach acids. Yet further, for a topically administered composition, the stabilizer can also include antagonists to skin acids.

The composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the lactoferrin composition to be released and absorbed by specialized cells, e.g., epithelial enterocytes and Peyer's patch M cells.

Further, the composition for topical administration which is combined with a semi-solid carrier can be further formulated into a gel ointment. A preferred carrier for the formation of a gel ointment is a gel polymer. Gel polymers prevent denaturation of the composition in the open skin by serum proteases. The gel formulation of the present invention also provides a controlled delivery system for lactoferrin or its activity on a wound site. Controlled delivery refers to drug release or activity release sufficient to maintain a therapeutic level over an extended period of time, such as up to 24 hours or more, preferably in the range of 1 to 12 hours. The present gel formulation increases the contact time of the lactoferrin at the wound site and provides a sustained release dosage form necessary to achieve a significant increase in the rate of wound healing. This is an important advantage because it permits less frequent application of the formulation to the wound and thereby permits fewer disturbances to the wound and its cellular components.

The gel formulation of the present invention has the advantage of adhering to a wound and conforming to irregular body or wound contours. The gels may be applied directly to a wound site or in conjunction with a compliant porous or microporous substrate, for example in the form of a coating, to be applied to the wound site. Gels have the further advantages of having a high water content (which keeps the wound moist), the ability to absorb wound exudate, easy application to a wound and easy removal by washing. Gels have a cool feeling when applied to a wound and thus can increase patient comfort and acceptance of the formulation, especially on sensitive wounds.

The aqueous gels of the present invention have different viscosities depending on the intended application of the gel. Viscosity is a measure of the resistance of a liquid to flow. It is defined as the ratio of the shearing stress to the rate of shearing. The shear stress is the resistance of the liquid to flow under the influence of an applied force, i.e., the molecular resistance within a body opposing an external force. The shear stress is defined as the ratio of the force to the area sheared. When a liquid is sheared, assuming laminar flow, the layers of the liquid move at different rates. The relative rate of motion of the layers is only one factor in the rate of shear. The other is the distance, or clearance between the shearing planes. Thus, shear rate is defined as the ratio of the velocity of the gel to the clearance. Viscosity has the dimensions of dynes/sec/cm². These dimensions are referred to as poise. The dimensions of viscosity referred to herein, unless otherwise indicated, are in centipoise (cP) as measured using a Brookfield viscometer. All viscosity values are at room temperature, e.g., 22° C.-25° C., unless otherwise indicated.

The amount of lactoferrin in the present invention may vary from about 1 μg to about 100 g of lactoferrin. In preferred embodiments, the composition of the present invention comprises a lactoferrin concentration of about 0.0001% to about 30%. More preferably, lactoferrin is orally administered in the range of 10 mg to 25 g or lactoferrin is topically administered in the range of 1 μg to 5 g. The lactoferrin may comprise lactoferrin or an N-terminal lactoferrin variant in which at least the N−1 terminal glycine residue is truncated and/or substituted.

More preferably, the composition of the present invention also contains metal chelators, for example, but not limited to ethylenediaminetetraacetic acid (EDTA), [ethylenebis (oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof. The amount of the metal chelator in the composition may vary from about 1 ng to about 1 g. A preferred metal chelator is EDTA.

The gel forming materials of the present invention may be water-soluble polymers capable of forming a viscous aqueous solution or non-water soluble, water swellable polymers (e.g., collagen), which can also form a viscous solution. Swellable polymers are those that absorb water rather than dissolve in water. Cross-linked forms of the polymer described herein may not be water soluble but may be water-swellable. Therefore, cross-linked forms of the polymer are within the scope of the present invention. Cross-linking refers to covalently bonding polymer chains together with a bifunctional reagent such as glutaraldehyde. Also, it is understood by those skilled in the art that certain polymers may have to be used in the salt form or partially neutralized in order to be made water soluble. For example, it is preferable to use hyaluronic acid as sodium hyaluronate to provide suitable water solubility.

In the aqueous gel formulations for topical or incisional wound healing, the polymer may be selected from the group consisting of vinyl polymers, polyoxyethylene-polyoxypropylene copolymers, polysaccharides, proteins, poly(ethylene oxide), acrylamide polymers and derivatives or salts thereof. It is understood that poly(ethyleneoxide) includes polyethylene glycol. In the gel formulations for use in healing wounds in the anterior chamber of the eye, the polymers may be the same except that it is not preferred to use the polyoxyethylene-polyoxypropylene copolymers or poly(ethylene oxide). Also, for anterior chamber use, it is preferred that the polymer is biodegradable, i.e., it will break down into harmless constituents that can be drained from or metabolized in the anterior chamber. In the low viscosity, aqueous formulations for use in ophthalmic wound healing, the gel forming polymers may be the same as for topical or incisional wound healing, except that poly(ethylene oxide) is not preferred to be used.

The vinyl polymers useful in the present invention may be selected from the group consisting of polyacrylic acid, polymethacrylic acid, polyvinyl pyrrolidone and polyvinyl alcohol. The polysaccharides useful in the present invention are selected from the group consisting of cellulose or cellulose derivatives, glycosaminoglycans, agar, pectin, alginic acid, dextran, starch, and chitosan. Starch occurs in two forms, α-amylose and amylopectin. The more water-soluble α-amylose is preferred. The glycosaminoglycans are selected from the group consisting of hyaluronic acid, chondroitin, chondroitin-4-sulfate, chondroitin-6-sulfate, dermatan sulfate, keratan sulfate, heparin sulfate and heparin. The glycosaminoglycans are used to enhance wound healing in combination with any other gel-forming polymer. The proteins useful in the present invention are selected from the group consisting of collagen, gelatin and fibronectin. The acrylamide polymers are polyacrylamide or polymethacrylamide polymers. Biocompatible polyacrylamide polymers are preferred. In further embodiments, carbomers are the preferred polyacrylamide polymer. Carbomers are synthetic high molecular weight polymers of acrylic acid cross linked with either alkyl esters of sucrose or pentaerythritol. Suitable commercially available grades of carbomer include Carbopol 910, Carbopol 934P, Carbopol 940, Carbopol 941, Carbopol 971P, Carbopol 974P, Carbopol 980, Carbopol 981, Carbopol 1342, Rheogic 252L, Rheogic 250H, and Hostacerin PN73.

In the gel formulation for topical or incisional wound healing, the viscosity may be within the range 1,000-12,000,000 cps at room temperature. It is preferred that the viscosity range be 50,000-2,000,000. In one embodiment of the present invention, the topical gel formulation may comprise 0.01-5% by weight polyacrylic acid having an average molecular weight of about 450,000-4,000,000. In a preferred embodiment, the polyacrylic acid is present at 0.5-1.5% by weight and has an average molecular weight of 2,000,000-4,000,000. The pH of the polyacrylic acid gel should be within the range 4.5-8 and more preferably in the range 6.5-7.5.

In another embodiment, the topical and incisional gel of the present invention may comprise 15-60% by weight of a polyoxyethylene-polyoxypropylene block copolymer having an average molecular weight of about 500-50,000. In a preferred embodiment, the block copolymer is present at 15-40% by weight and has an average molecular weight in the range 1,000-15,000. The block copolymers used in the present invention are commonly known as Pluronics. Preferred Pluronics are Pluronic F88 and F127.

In a further embodiment, the topical or incisional gel may comprise 1 to 20% by weight of a cellulose polymer having a molecular weight of about 50,000 to 700,000. In a preferred embodiment, the cellulose polymer is present at 2-8% by weight and has an average molecular weight in the range 80,000-240,000. Preferred cellulose polymers are hydroxypropylmethyl cellulose (HPMC), carboxymethyl cellulose (CMC) and methyl cellulose (MC).

In a further embodiment, the topical and incisional gel may comprise 0.5-10% by weight of hyaluronic acid having an average molecular weight in the range 500,000 to 8,000,000. In a preferred embodiment, the hyaluronic acid is present at 1.5-6.0% by weight and the average molecular weight is greater than 1,000,000.

Acrylamide polymers may be useful for all types of wound healing, particularly in the anterior chamber of the eye. An absorbable acrylamide polymer, such as polyacrylamide, may be a good substitute for present carrier systems used in ophthalmic applications, such as hyaluronic acid. The acrylamide polymers may have an average molecular weight in the range 1-13 million, preferably about 4-6 million. The weight percent of the acrylamide polymer in the gel may be 2-5%, preferably 3.5-4.5%. Substituted acrylamide polymers, such as methyl and alkyl substituted polymers are also within the scope of the present invention.

For use in the anterior chamber of the eye, an acrylamide gel delivery system has the following characteristics: any products of the dissolution or degradation of the delivery matrix are nontoxic and do not clog the trabecular mesh work;

the gel is optically transparent; and the gel can be left in the anterior chamber without causing adverse clinical effects such as an unacceptable increase in ocular pressure.

It will be readily apparent to one skilled in the art that the desired viscosity range may be achieved by varying the molecular weight and percent concentration of the polymer in the formulation. For example, a gel having a low viscosity may be achieved by using a low molecular weight polymer or a lower percent concentration or a combination of the two. A high viscosity gel may be achieved by using a higher molecular weight polymer and a higher percent concentration. Intermediate viscosities may be achieved by varying the molecular weight and percent concentration accordingly.

The low viscosity solution may comprise 0.01-2.0% by weight polyacrylic acid having an molecular weight of about 100,000-4,000,000. In a preferred embodiment, the polymer is present at 0.05-0.5%. In another embodiment, this dilute viscous solution may comprise 2-40% by weight of a polyoxyethylene-polyoxypropylene copolymer having an average molecular weight of 500-500,000. Preferably, the concentration is 2-20% and the molecular weight is 1,000-15,000. Alternatively, the dilute viscous solution may comprise a cellulose polymer at 1-20% and having a molecular weight of about 80,000-240,000. It is preferred that the concentration be in the range of 1-10%. In a further embodiment, the dilute viscous solution may comprise 0.5-5.0% by weight hyaluronic acid having an average molecular weight of about 500,000-8,000,000. Preferably, the concentration is 0.5-2.0% and the average molecular weight is 1,000,000-6,000,000. If the dilute viscous solution is to be used as eye drops, it is preferred that the viscosity be in the range 1-100 cps. If it is used for other applications, such as soaking a bandage, then any viscosity in the range 1.0-5,000 will be suitable.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules, gel ointments and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

D. TREATMENT OF WOUNDS

In accordance with the present invention, a lactoferrin composition provided in any of the above-described pharmaceutical carriers is orally, topically, or parenterally administered to a subject suspected of or having a wound. One of skill in the art can determine the therapeutically effective amount of the composition to be administered to a subject based upon several considerations, such as absorption, metabolism, method of delivery, age, weight, disease severity and response to the therapy. Oral administration of the composition includes oral, buccal, enteral or intragastric administration. It is also envisioned that the composition may be used as a food additive. For example, the composition is sprinkled on food or added to a liquid prior to ingestion. Topical administration of the composition includes topical, dermal, epidermal, or subcutaneous administration. Parenteral administration includes, but is not limited to intramuscular, intravenous, intraperitoneal, intraoccular or intraarticular administration or administration into a surgical field.

The present invention is designed for the treatment of any type of wound, which includes, but is not limited to skin wound, internal wound, gastrointestinal wound, oral wound, bone wounds, ophthalmic wound, surgical wound, or any combination thereof. Wounds can be found on but not limited to skin, internal organs, stomach and intestines (gastrointestinal), oral mucosa, and eye (ophthalmic wounds, e.g., corneal ulcers, radiokeratotomy, corneal transplants, epikeratophakia and other surgically induced wounds in the eye). Depending on the process that causes the wounds, wounds can also be classified as but are not limited to incisional wounds, excisional wounds, diabetic ulcers, venous stasis ulcers, decubitus or pressure ulcers, chemical wounds, and burn wounds.

A further embodiment of the present invention is administering the inventive composition to treat skin wounds. Skin wounds further comprise but are not limited to full-thickness wounds and partial-thickness wounds. Full-thickness wounds involve the complete removal of epidermis and dermis to the depth of fascial planes or subcutaneous fat. In the loose-skinned species, the thin musculature of the *panniculus carnosus*, which firmly adheres to the base of the dermis, is usually removed as well. In partial-thickness wounds a substantial amount of dermis, mostly reticular, is left behind, and, more importantly, the bases of most epidermal appendages (sebaceous and sweat glands, hair follicles) remain intact.

Yet further, a wound can be further defined as an acute wound. Acute wounds have a relatively rapid rate of healing, especially in healthy subjects. However, in the elderly or immunocompromised healing can be prolonged. Healing is also prolonged if the wound becomes infected. Preferred acute wounds that are to be treated with the present composition include, but are not limited to partial-thickness burns, lacerations, bullet wounds or infected wounds.

A wound is also further defined as a chronic wound. Examples of chronic wounds or chronic ulcers include, but are not limited to diabetic ulcers, venous stasis ulcers, decubitus or pressure ulcers. Yet further, chronic wounds can also include infected wounds. Chronic wounds are wounds that do not repair or do so extremely slowly, and show partial or total lack of structural organization and functional coordination with normal tissue. Chronic wounds or chronic ulcers can be broadly classified into three major types: diabetic ulcers, venous stasis ulcers, decubitus or pressure ulcers. Diabetic ulcers often occur on a foot. Chronic diabetic state and poor glucose control results in poor peripheral circulation and microcirculation due to progressive arteriosclerosis; neuropathic changes that result in an insensate extremity prone to trauma; and intrinsic defects in the wound healing process that may include reduced abundance and response to cellular growth factors. In the case of venous ulcers, venous hypertension causes disturbed microcirculation and pathological changes of the capillaries, elevated persistent levels of pro-inflammatory cytokines and proteases. Fibroblast senesce and respond less to growth factors, which distribute unfavorably. Proteolytic enzymes and their inhibitors are imbalanced. Pressure ulcers occur when skin is under pressure without movement to allow blood flow for 8-12 hours.

In a preferred embodiment of the present invention, the inventive composition (lactoferrin alone or lactoferrin in combination with a metal chelator) is administered in an effective amount to seal, to close, to improve or to repair the wound. Also, it is envisioned that the composition of the present invention can also decrease, reduce, or inhibit, bacterial infections of the wound, which aid in the healing process of a wound.

Treatment regimens may vary as well, and often depend on wound type, wound location, wound and/or healing progression, and health and age of the patient. Obviously, certain types of wounds will require more aggressive treatment, while at the same time, certain patients cannot tolerate more taxing protocols. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. In a further embodiment, the composition is given in a series of doses. The series of doses may be administered daily, or multiple times a day, weekly, or multiple times a week, or monthly, or multiple times a month. Thus, one of skill in the art realizes that depending upon the wound type, location, health of the subject, etc., the lactoferrin composition of the present invention may be administered for any given period of time until the wound is healed at least by 5%, 10%, 20%, 30%, 40%, 50%, 55%, 60%, 65%, 70%, 75%, 80%, 85%, 90%, 95% or 100% or any range in between.

For topical administration, the gel formulation of the present invention may be used to coat fibers of an absorbent gauze dressing to form a wound healing bandage which may then be placed on a wound. The low viscosity formulation is preferred for this use. The wound healing bandage may be prepared by soaking a gauze dressing with an aqueous gel solution containing lactoferrin having wound healing activity. The bandage can then be applied to the wound so that the coated fibers of the gauze contacts the wound and stimulate the rate of wound healing.

In those applications where the present invention is a gel that is applied to an internal or incisional wound, it is preferred that the gel forming polymer be biodegradable. The naturally occurring polymers are generally biodegradable. Examples of these are collagen, the glycosaminoglycans, gelatin and starch. The cellulosics are not biodegradable. The synthetic polymers such as the vinyl polymers are not degradable. The biodegradability of the polymers described herein is well known to those skilled in the art.

A further embodiment of the present invention is a method of treating a wound comprising the step of supplementing the local immune system by increasing the amount of lactoferrin in the vicinity of the wound. Preferably, the lactoferrin is administered topically to the wound.

Yet further, the present invention also provides a method of treating a wound comprising the step of supplementing the systemic immune system by increasing the amount of lactoferrin in the systemic circulation. Preferably, the lactoferrin is administered via a parenteral route, which includes, but is not limited to intramuscular, intravenous, intraperitoneal, intraocular, intraarticular or into a surgical field.

Still yet, a further embodiment is a method of treating a wound comprising the step of supplementing the mucosal immune system by increasing the amount of lactoferrin in the gastrointestinal tract of the subject.

In further embodiments, the present invention provides a method of enhancing the immune system of a subject suffering from a wound by administering to the subject a lactoferrin composition. Depending upon the mode of administration, different arms of the immune system are enhanced. For example, topical administration of the composition results in enhancement of the local immune system, i.e., in the vicinity of the wound. Parenteral administration of the composition results in enhancement of the systemic immune system. Yet further, oral administration of the composition results in enhancement of the mucosal immune system, which can also result in systemic effects as well. In further embodiments, the lactoferrin composition is administered in combination with a metal chelator, for example EDTA.

It is envisioned that the immune system, whether local, systemic or mucosal, is enhanced by lactoferrin stimulating cytokines and/or chemokines. Exemplary cytokines include interleukin-18 and GM-CSF in the gastrointestinal tract, which are known to enhance immune cells or stimulate production of immune cells. For example, interleukin-18 enhances natural killer cells or T lymphocytes, which can kill bacteria infecting a wound. In specific embodiments, interleukin-18 (IL-18) enhances CD4+, CD8+ and CD3+ cells. It is known by those of skill in the art that IL-18 is a $Th_1$ cytokine that acts in synergy with interleukin-12 and interleukin-2 in the stimulation of lymphocyte IFN-gamma production. Other cytokines or chemokines may also be enhanced for example, but not limited to IL-12, IL-1b, MIP-3α, MIP-1α, or IFN-gamma. Other cytokines or enzymes may be inhibited for example, but not limited to IL-2, IL-4, IL-5, IL-10, TNF-α, or matrix metalloproteinases. It is further contemplated that IL-18 or GM-CSF stimulate the production or activity of cells involved in wound repair, for example, but not limited to keratinocytes, endothelial cells, dendritic cells, fibroblasts, and myofibroblasts. Yet further, it is envisioned that lactoferrin inhibits the production of TNF-alpha, which inhibits cells involved in inflammation.

It is further envisioned that supplementing the local immune system in a subject by administering topically a therapeutically effective amount of a lactoferrin composition in the vicinity of the wound can result in the killing of bacteria infecting the wound. Still further, topical administration of a lactoferrin composition may stimulate the production of a cytokine or a chemokine. Exemplary cytokines that can be stimulated by lactoferrin include, but are not limited to interleukin-18 (IL-18), interleukin-12 (IL-12), granulocyte/macrophage colony-stimulating factor (GM-CSF), and gamma interferon (IFN-γ). Exemplary chemokines include, but are not limited to macrophage inflammatory protein 3 alpha (MIP-3α), macrophage inflammatory protein 1 alpha (MIP-1α), or macrophage inflammatory protein beta (MIP-10).

The lactoferrin composition of the present invention can also result in inhibition of a cytokine or chemokine. The cytokines include, but are not limited to interleukin-2 (IL-2), interleukin-4 (IL-4), interleukin-5 (IL-5), interleukin-10 (IL-10), and tumor necrosis factor alpha (TNF-α). Still further, the lactoferrin composition can also inhibit the production of matrix metalloproteinases (MMPs).

In further embodiments, cytokines, for example, interleukin-18 or granulocyte/macrophage colony-stimulating factor, can stimulate the production or activity of immune cells. The immune cells include, but are not limited to T lymphocytes, natural killer cells, macrophages, dendritic cells, and polymorphonuclear cells. More specifically, the polymorphonuclear cells are neutrophils and the T lymphocytes are selected from the group consisting of CD4+, CD8+ and CD3+ T cells.

In a further embodiment, cytokines, for example, interleukin-18 or granulocyte/macrophage colony-stimulating factor, can also stimulate the production or activity of cells involved in wound repair. The cells involved in wound repair include, but are not limited to keratinocytes, endothelial cells, fibroblasts, dendritic cells, and myofibroblasts. The inhibition of TNF-alpha further inhibits the migration and maturation of dendritic cells. The dendritic cells can be Langerhans cells.

E. COMBINATION TREATMENTS

In order to increase the effectiveness of the composition of the present invention, it may be desirable to combine the composition of the present invention with other agents effective in the treatment of wounds, such as growth factors, skin replacement therapy, enzymatic and surgical debridement, moist wound dressings, cleansers, antibiotics. Such wound healing agents are capable of negatively affecting a wound in a subject, for example, by enhancing the growth rate of skin cells, augmenting the blood supply to skin cells, promoting an immune response against bacteria infecting the wound, killing bacteria, cleaning ischemic tissue, promoting the closure of the wound. More generally, these other wound healing agents are provided in a combined amount effective to promote the healing of a wound. This process may involve administering the composition of the present invention and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the lactoferrin composition and the other includes the second agent(s).

Alternatively, the composition of the present invention may precede or follow the other wound healing agent treatment by intervals ranging from minutes to weeks. In embodiments where the other wound healing agent and inventive composition are administered or applied separately to the wound, one would generally ensure that a significant period of time did not expire between the time of each delivery, such that the agent and human lactoferrin composition would still be able to exert an advantageously combined effect on the wound. In such instances, it is contemplated that one may contact the wound with/administer both modalities within about 1-14 days of each other and, more preferably, within about 12-24 hours of each other. In some situations, it may be desirable to extend the time period for treatment significantly, however, where several days (2, 3, 4, 5, 6 or 7) to several weeks (2, 3, 4, 5, 6, 7 or 8) lapse between the respective administrations.

1. Growth Factors

Wound healing therapies include growth factor based treatments. Examples include, but are not limited to Regranex™ (Becaplermin-BB gel), AuTolo-Gel (autologous activated platelet releasate), Procuren (autologous thrombin-induced platelet releasate). Growth factors act without limitation by promoting granulation or the formation of new highly vascularized connective tissue; stimulating proliferation, differentiation and migration of epithelial cells, vascular endothelial cells and other skin cells; enhancing the production of collagen, collagenase, and extracellular matrix.

2. Skin Replacement Therapy

Examples include but are not limited to Apligraf (bilayered living skin), Trancyte (Human fibroblast-derived temporary skin substitute), Dermagraf (permanent, one-layer skin substitute), Epicel (living one-layer artificial skin), Integra (collagen-based skin regeneration template), AlloDerm (single-layer artificial skin made from human cadavers), CCS (living, cultured, artificial skin).

3. Enzymatic and Surgical Debridement

Debridement is a process or procedure to clean ischemic or dead tissue. Enzymatic debriders include Accuzyme papain-urea debriding ointment and Collagenase Santyl. Surgical debridement refers to physical removal of at least part of the ischemic or dead tissue in a wound. Debridement may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. Enzymatic debridement treatments may be of varying dosages as well. It is further contemplated that the present invention may be used in conjunction with enzymatic or surgical debridement.

4. Dressings

Wound healing therapies include a variety of treatments based on dressings. Dressing categories include but are not limited to amorphous hydrogels, hydrogel sheets, absorptives, alginates, biological and synthetic dressings, collagens, composites, contact layers, elastic gauzes, foams, gauzes and non-woven dressings, hydrocolloids, impregnated dressings, silicone gel sheets, silver dressings, transparent films, wound fillers 5. Cleansers Examples include but are not limited to Biolex, Lamin, Wound Wash Saline, Techni-Care, CarraKlenz, DiaB Klenz, MicroKlenz, RadiaCare Klenz, UltraKlenz, Comfee Sea-Clens, Optipore Sponge, Saf-Clens, Shur-Clens, Dermagran, DermaKlenz, Dumex, Gene Klenz, GRX, Allclenz, Restore, Hyperion, Medi Tech, Skintegrity, MPM Antimicrobial, ClinsWound, Septicare, Lobana Saline.

6. Antimicrobials

Examples of include but are not limited to Sulfamylon Cream, Thermazene Cream (1% silver sulfadiazine), cadexomer-iodine pads or gel. Examples of intravenous antimicrobials include but are not limited to imipenem/cilastatin, β-lactam/β-lactamase inhibitors (ampicillin/sulbactam, piperacillin/tazobactam), and broad-spectrum cephalosporins (cefoxitin, ceftizoxime, ceftazidime). Other examples include, but are not limited to Bensal HP, Barri-Care, Care-Creme, Formula Magic, Baza, Micro-Guard, Ca-Rezz, Diabet-X products, Mitrazol Powder, PiercingCare, Triple Care products, and various antifungal creams and powders.

7. Compression

Dynamic compression examples, include pumps and sleeves such as but not limited to ArtAssist, ArterialFlow, EdemaFlow, PulStar, Circulator Boot, Flowplus, Flowpress, Flowtron. Static compression include but are not limited to leg wrappings, gloves, socks, leg wears, leg supports, arm sleeves, stasis pads, compression hosieries, non-elastic bands, high compression bandages, zinc impregnated bandages, elastic bandages.

8. Oxygen Therapy

Examples of systemic hyperbaric oxygen therapy include but are not limited to compartments for one patient to lay down, for one patient to sit up to 25 degree angle, for one patient to sit up to 90 degree angle, for more than one patient to be treated simultaneously. Examples of topical hyperbaric oxygen therapy include but are not limited to disposable topical hyperbaric oxygen systems for extremity ulcers, disposable topical hyperbaric oxygen systems for decubitis, post-op and trauma wounds.

9. Hydrotherapy, Electric Therapy

Examples include but are not limited to dry hydrotherapy machines; non-contact thermal wound care systems for use on partial- and full-thickness wounds that maintain warmth and humidity in the wound area; systems that provide non-thermal, pulsed high frequency, high peak power, electromagnetic energy to treat edema and pain in acute and chronic wounds; systems that use controlled, localized negative pressure and support for moist wound healing; pulsatile irrigators with controllable pressures below 15 psi for site-specific treatment of various wounds with variety of tips; various wound irrigation and whirlpool systems.

10. Nutritional Therapy Products

Examples include but are not limited to isotonic, high-protein, fiber-containing tube feedings to support wound healing; high-protein, cholesterol-free nutritional supplements.

11. Cohesives, Glues, Sealants, Patches

Examples include but are not limited to Dermabond, CoStasis, CoSeal, BioGlue, FibRx, FocalSeal, FloSeal, AutoSeal, Indermil, Syvek, LiquiSheild, LiquiBand, Quixil, CryoSeal, VIGuard Fibrin Sealant, and various tapes, closures, and securement products.

12. Topical Wound Healing Promoters

Examples include but are not limited to topical aerosols which stimulate the capillary bed of chronic wounds; skin protectants with zinc-nutrient formulations; topical gels to help scars feel softer and smoother; hydrophilic ointments that cleanse degraded proteins, promote healthy granulation, control local inflammation and reduce wound odors; oil-and-water wound dressing emulsions that selectively recruit macrophages.

13. Other Biotherapy Agents

Adjuvant therapy may also be used in conjunction with the present invention. The use of adjuvants or immunomodulatory agents include, but are not limited to tumor necrosis factor; interferon alpha, beta, and gamma; IL-2 and other cytokines; F42K and other cytokine analogs; or MIP-1, MIP-1beta, MCP-1, RANTES, and other chemokines.

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of rhLF Carbomer Gels

Polyacrylic acid or Carbomer gels of grade 980 (Carbopol 980) were prepared according to the present invention.

Six 30-gram rhLF gels were made having theoretical label strengths of 0%, 0.1%, 0.3%, 1%, 2.5%, and 8.5%. The gels had the general formula as shown in Tables 1 and 2.

TABLE 1

General Formula of rhLF Gels

| | %(ww) | 30 g batch (g) |
|---|---|---|
| Phosphate Buffer with rhLF** | 86.6700 | 26.00** |
| Carbopol 980 | 1.0000 | 0.30 |
| Edetate Disodium, Dihydrate, USP | 0.1000 | 0.03 |
| Phenoxyethanol | 1.0000 | 0.30 |
| Glycerin, USP | 4.0000 | 1.20 |
| Propylene Glycol, USP | 5.0000 | 1.50 |
| Dimethicoone NF 350 centistokes | 0.4000 | 0.12 |
| Citric Acid, Monohydrate Granular, USP | 0.0956 | 0.03 |
| 20% Sodium Hydroxide | q.s. to pH 6.5-7.5 | q.s. to pH 6.5-7.6 |
| Purified Water, USP | q.s to 100% | q.s. to 30 g |

**See Total Volume in Table 2

TABLE 2

Volume of Phosphate Buffer and rhLF Stock Used to Prepare the Gels

| RhLF (% w/w) | rhLF wt in 30 g batch (g) | Volume of Stock (ml)* | Volume of Phos. Buf (ml) | **Total Volume Added (ml) |
|---|---|---|---|---|
| 0 | 0 | 0 | 26 | 26 |
| 0.1 | 0.03 | 0.3 | 25.7 | 26 |
| 0.3 | 0.09 | 039 | 25.1 | 26 |
| 1 | 0.3 | 3 | 23 | 26 |
| 2.5 | 0.75 | 7.5 | 18.5 | 26 |
| 8.5 | 2.55 | 25.5 | 0.5 | 26 |

**100 mg/ml rhLF in phosphate buffer Lot # E01764-03L

The gels were mixed in pre-weighed 125 ml stainless steel beakers and mixed using a programmable Caframo Mixer (Model BDC1850, Ontario, Canada). The usual mixing rate was 600 rpm using a stainless steel stirring rod with ½" diameter blades. The gels were made by adding Carbopol 980 to phosphate buffer (6 mM sodium phosphate monobasic monohydrate, 9 mM sodium phosphate dibasic heptahydrate, 50 mM NaCl, pH 7). The volume of phosphate buffer used to make the initial gel is shown in the $4^{th}$ column (heading "Volume of Phos. Buf) in Table 2. After Carbopol 980 was fully hydrated (usually within 45 minutes), the glycerin, propylene glycol, and phenoxyethanol were added followed by citric acid and then edetate disodium. Finally, the dimethicone was added. The pH of these gels was in the range of pH 3-3.5. At this point, 20% sodium hydroxide was added to raise the pH. When the pH reached about 6, the rhLF was added (as shown in Table 2, $3^{rd}$ column "Volume of Stock"). The pH was then raised to 7. The only deviation from the above procedure was with the 8.5% w/w rhLF gel. Since the volume of stock needed was large, the Carbopol 980 was added directly to 26 ml of phosphate buffer containing rhLF. Thus, the rhLF in the 8.5% w/w/ gel was exposed to a pH of 3-3.5 for a period of approximately 30-45 minutes.

A Brookfield DV-III+Rheometer was used to measure the viscosity of the gels in triplicate (0.5 ml of each gel). The conditions were: Temperature: 25° C.; Equilibration Time: 5 min; Spin Rate: 1.7 RPM; Spin Time: 5 min. Results are shown in Table 3.

TABLE 3

Gel Viscosity

| rhLF Gel | Rep 1 (cP) | Rep 2 (cP) | Rep 3 (cP) | Average Viscosity | SD | % RSD |
|---|---|---|---|---|---|---|
| Placebo | 16634 | 16517 | 16751 | 16634 | 117 | 0.70 |
| 0.10% | 13190 | 13132 | 13482 | 13268 | 188 | 1.41 |
| 0.30% | 16459 | 16400 | 16634 | 16498 | 122 | 0.74 |
| 1.00% | 17509 | 17334 | 17626 | 17490 | 147 | 0.84 |
| 2.50% | 19494 | 19611 | 19669 | 19591 | 89 | 0.46 |
| 8.50% | 45641 | 45758 | 44240 | 45213 | 845 | 1.87 |

For the standard curve, 1.563-25 µg/ml rhLF standards were prepared by diluting the 100 mg/ml rhLF stock (lot# E01764-03L) in de-ionized (DI) water. All active samples were taken from the top, middle, and bottom of 3 ml aluminum crimped tubes and were prepared at a theoretical concentration of approximately 10 µg/ml rhLF in DI water. All active gels passed content uniformity specification (+/−10%).

Example 2

Bioavailability of rhLF from Carbomer Gels on Full-Thickness, Open Wounds

Five Groups of three ICR male mice (weighing 22±2 gms) were used. Under hexobarbital (90 mg/Kg, IP) anesthesia, the shoulder and back region was shaved. A sharp punch (ID 12 mm) was used to remove the skin including *panniculus carnosus* and adherent tissues.

A low and a high dose of recombinant human lactoferrin (rhLF) administered topically (carbopol-980 gel formulation) or one dose administered intravenously (liquid solution) were applied immediately after the injury, as indicated in Table 4. RhLF doses were given to 20-gram mice immediately following wound injury. The following doses were used: (1) Placebo, 0.04 ml/mouse, topical; (2) 50 mg/Kg, 0.04 ml of a 2.5% gel; (3) 170 mg/Kg, 0.04 ml of an 8.5% gel. Three animals (one male two females) were sacrificed at 0, 15, 30, 60, 120, and 240 minutes following application of test compound. Sacrificed animals were exsanguinated; blood was anticoagulated using EDTA, plasma was separated from EDTA blood, and the samples were quickly frozen and stored at −80.

TABLE 4

Bioavailability of rhLF - Experimental Design and Methods

| Treatment | Route | Dose | Sex | \multicolumn{7}{c}{Plasma Preparation Minutes after Treatment} |
|---|---|---|---|---|---|---|---|---|---|---|
| | | | | 0 | 5 | 15 | 30 | 60 | 120 | 240 |
| None | None | 0 | M | A1 | — | — | — | — | — | — |
| | | | F | A1 | — | — | — | — | — | — |
| | | | F | A1 | — | — | — | — | — | — |
| Vehicle (Placebo gel) | TOP | 0.04 ml/mouse | M | — | B1 | — | — | B2 | B3 | — |
| | | | F | — | B1 | — | — | B2 | B3 | — |
| | | | F | — | B1 | — | — | B2 | B3 | — |
| PT# 1028377 (AGX-6) (rhLF gel) | TOP | 50 mg/kg | M | — | C1 | C2 | C3 | C4 | C5 | C6 |
| | | | F | — | C1 | C2 | C3 | C4 | C5 | C6 |
| | | | F | — | C1 | C2 | C3 | C4 | C5 | C6 |
| | TOP | 170 mg/kg | M | — | D1 | D2 | D3 | D4 | D5 | D6 |
| | | | F | — | D1 | D2 | D3 | D4 | D5 | D6 |
| | | | F | — | D1 | D2 | D3 | D4 | D5 | D6 |
| PT# 1023296-ADD (AGX-1) (rhLF) | IV | 5 mg/kg | M | — | E1 | E2 | E3 | E4 | E5 | E6 |
| | | | F | — | E1 | E2 | E3 | E4 | E5 | E6 |
| | | | F | — | E1 | E2 | E3 | E4 | E5 | E6 |

Concentrations of rhLF in plasma were determined using the BIOXYTECH® Lacto F EIA kit from OXIS Health Products, Inc, following the directions provided by manufacturer. Results were obtained by measuring absorbance at 490 nm wavelength.

The peak plasma concentration attained was calculated relative to peak rhLF plasma concentrations following IV administration. The dose adjusted peak concentration of rhLF following topical gel application on open full-thickness wounds at doses of 50 mg/Kg (151 ng/ml) and 170 mg/Kg (75.1 ng/ml) was less than 0.5% of the normalized peak concentration following 5 mg/kg IV rhLF (92,455.1 ng/ml) (see Table 5). The total plasma bioavailability, as calculated by the mean area under the concentration curve (AUC) normalized to 170 mg/Kg, of the plasma rhLF time course with the 50 mg/Kg topical gel dose was 18.4 µg.min/ml, indicating an absolute systemic bioavailability of less than 0.5%. The AUC for the 170 mg/Kg topical gel dose was 9.6 µg·min/ml, also corresponding to an absolute systemic bioavailability value of less than 0.5% (See Table 5).

TABLE 5

Pharmacokinetics of topically-applied rhLF to open wounds in mice

| | Low dose topical gel (50 mg/kg) | High dose topical gel (170 mg/kg) | Intravenous rhLF solution (5 mg/kg) |
|---|---|---|---|
| Peak plasma concentration (ng/mL) | 44 | 75 | 2,719 |
| Time achieved (min) | 60 | 60 | 5 |
| Amount-normalized* (ng/mL) | 151 | 75 | 92,456 |
| Normalized % of IV | 0.2% | 0.1% | NA |
| AUC (µg · min/mL) | 5.4 | 9.6 | 152 |
| AUC-N (µg · min/mL)** | 18.4 | 9.6 | 5,174 |
| Absolute bioavailability | 0.4% | 0.2% | NA |

*Values normalized to 170 mg/kg
**AUC calculated with values normalized to 170 mg/kg.

Example 3

Efficacy of rhLF Carbopol Gels in Wound Healing Experiments

RhLF carbopolymer gels were applied at concentration strengths of 2.5% and 8.5% directly to full thickness, open wounds in normal and diabetic db/db mice. Diabetic (db/db) mice express lower levels of several growth factors and receptors, accounting, at least in part, for a reduced rate of healing Mice were anesthetized, the shoulder and back region of each animal was shaved, and a sharp punch (ID 12 mm) was used to remove the skin including *panniculus carnosus* and adherent tissues (open, full-thickness wounds). Different doses of rhLF were applied topically to the wounds (0.02 ml per wound) once per day for 11 days for normal mice or 20 days for diabetic db/db mice to compare the rates of healing with those of negative controls. The negative control was placebo gel. At several time points, the wound area was traced onto clear plastic and was measured with an Image Analyzer.

The incidence of animals reaching 75% wound closure was assessed and differences compared using Fisher's exact test. Differences were considered of statistical significance at p<0.05 levels. Calculated time to 50% wound closure (CT-50) was measured via polynomial equations (2 orders) and differences assessed with the Student t test for significance.

FIG. 1 shows rhLF gels ranging from 0.1% to 8.5% mediated an improvement in the incidence of 75% wound closure of 77% in normal mice at day 12 (p<0.0) and of 66% in diabetic db/db mice at day 15 (p<0.05). Table 6 below shows individual values at each concentration for normal mice in terms of incidence of 75% wound closure and calculated time to 50% wound closure (CT-50).

TABLE 6

A Broad Range of RhLF Gel Strengths Accelerate Wound Healing in Normal Mic

75% Incidence on Day 12

| Treatment | n | Number of Animals | Percent (%) | % Healing on Day 12 | CT50 (Days) |
|---|---|---|---|---|---|
| Placebo gel | 7 | 1 | 14 | 65.8 | 7.1 |
| 0.1% gel (0.02 mg) | 7 | 7 | 100 (p = 0.0047) | 90.6 (p < 0.0001) | 4.4 (p = 0.0079) |
| 0.3% gel (0.06) | 7 | 6 | 86 (p = 0.0291) | 86.5 (p = 0.001) | 3.9 (p = 0.0507) |
| 1.0% gel (0.2 mg) | 7 | 5 | 71 (p = 0.1026) | 88.6 (p = 0.001) | 4.6 (p = 0.0392) |
| 2.5% gel (0.5) | 7 | 7 | 100 (p = 0.0047) | 90.3 (p < 0.0001) | 4.4 (p = 0.0148) |
| 8.5% gel (1.7) | 7 | 7 | 100 (p = 0.0047) | 93.2 (p < 0.0001) | 3.5 (p = 0.0024) |

Based on these results, it is envisioned that topical, oral, or parenteral lactoferrin results in the killing of bacteria infecting a wound, in the stimulation of IL-18, IL-12, GM-CSF, MIP-1α, MIP-1β, MIP-3α, or IFN-γ, and in the inhibition of IL-2, IL-4, IL-5, IL-10, TNF-α, or matrix metalloproteinases. It is further envisioned that IL-18 or GM-CSF stimulate the production or activity of immune cells and cells involved in wound repair, and that TNF-alpha inhibits cells involved in inflammation.

Example 4

Wound Healing Time Course of rhLF, CGS-21680, and Regranex™ in Normal Mice

Groups of 7 ICR male mice were anesthetized, the shoulder and back region of each animal was shaved, and a sharp punch (ID 12 mm) was used to remove the skin including *panniculus carnosus* and adherent tissues. The wound area, traced onto clear plastic sheets on days 3, 5, 7, 9 and 11 or 12, was quantitated with an Image Analyzer.

RhLF solution, vehicle (buffer), or a positive control (RhPDGF) were applied topically immediately following injury and once daily thereafter for a total of 10 or 11 consecutive days. The unpaired Student's t test was applied for comparison between treated and vehicle group at each measurement time point. Differences were considered statistical significant at P<0.05. RhPDGF (recombinant human Platelet Derived Growth Factor-BB, Regranex™, becaplermin), which is presently the only available biological treatment in the market for chronic wounds (diabetic neuropathic ulcers), was used as a positive control at the approved strength of 100 micrograms/gram (0.01%). CGS-21680 is an an adenosine A2A receptor agonist that was also used as a positive control since it was previously described as being very effective in promoting wound healing and in fact to promote more rapid wound healing than Regranex™.

Figure 2A:
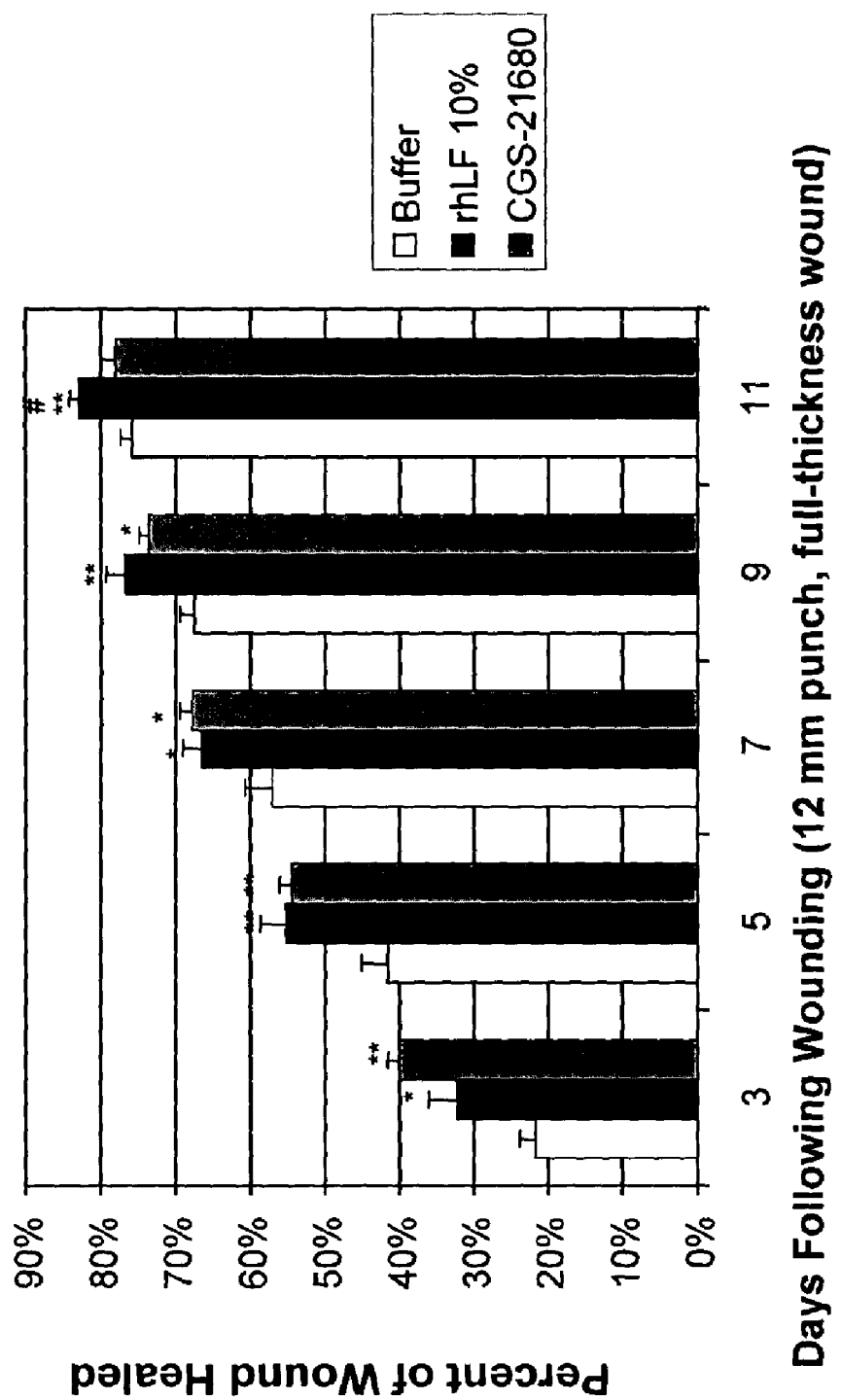
FIG. 2A and FIG. 2B show the time course of wound healing with and without topical administration of recombinant human lactoferrin solution in healthy mice. CGS-21680 (FIG. 2A) or Regranex™ (FIG. 2B) was used as a positive control.
Figure 2B:
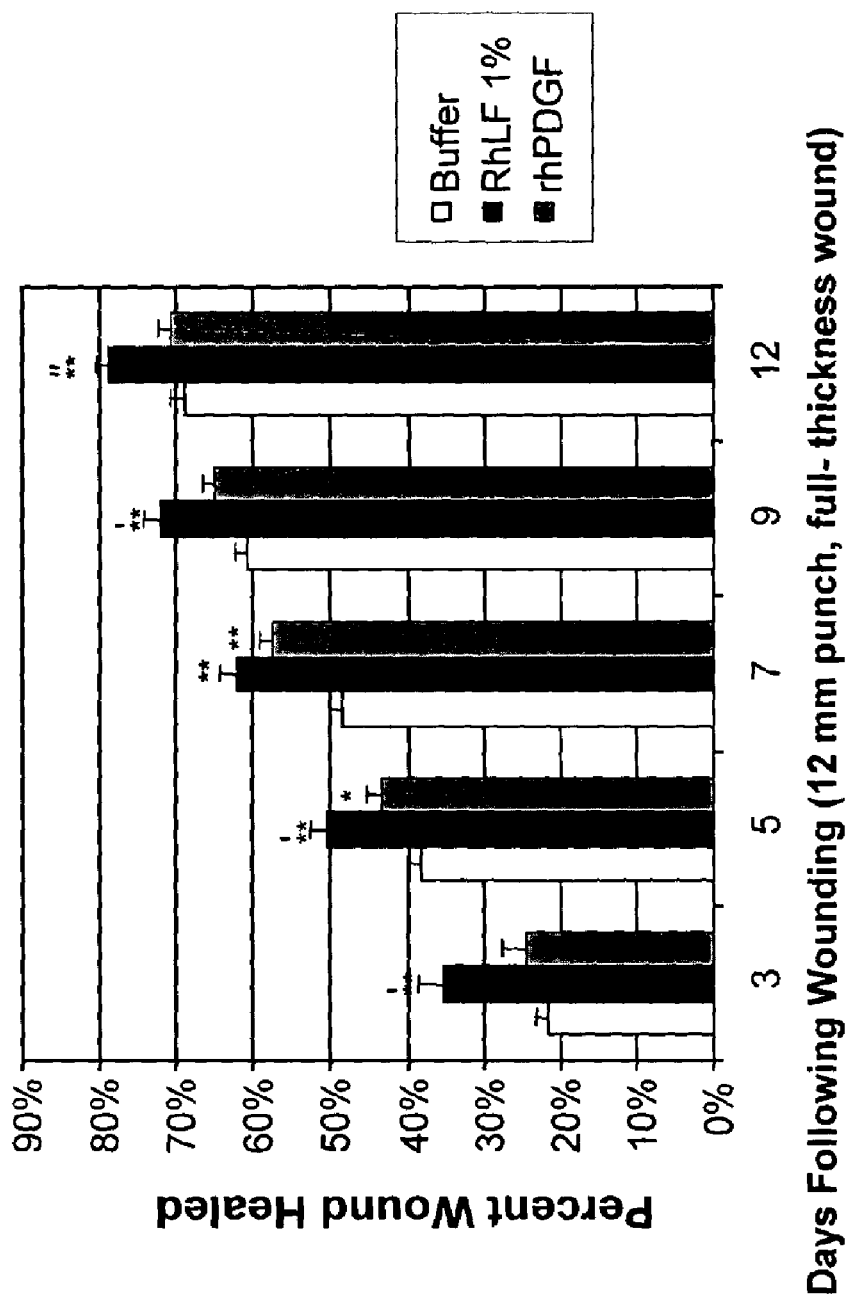

FIG. 2A indicates that rhLF exerted a comparable healing effect to that of CGS-21680, suggesting that rhLF promotes more rapid wound repair than Regranex™ (rhPDGF, Becaplermin). FIG. 2B confirms that rhLF promotes a greater extent of wound healing as compared to Regranex™.

Based on these results, it is envisioned that topical, oral, or parenteral lactoferrin results in the killing of bacteria infecting a wound, in the stimulation of IL-18, IL-12, GM-CSF, MIP-1α, MIP-1β, MIP-3α or IFN-γ, and in the inhibition of IL-2, IL-4, IL-5, IL-10, TNF-αt, or matrix metalloproteinases. It is further envisioned that IL-18 or GM-CSF stimulate the production or activity of immune cells and cells involved in wound repair, and that TNF-alpha inhibits cells involved in inflammation.

Example 5

Efficacy of rhLF Topical Solution vs. Regranex™ in Wound Healing Experiments

Mice were anesthetized, the shoulder and back region of each animal was shaved, and a sharp punch (ID 12 mm) was used to remove the skin including *panniculus carnosus* and adherent tissues (open, full-thickness wounds). Different doses of rhLF were applied topically to the wounds (0.02 ml per wound) once per day for 11 days for normal mice or 20 days for diabetic db/db mice to compare the rates of healing with those of negative and positive controls. Negative control or placebo was rhLF vehicle (a PBS solution). Positive control was RhPDGF (recombinant human Platelet Derived Growth Factor-BB, Regranex™, becaplermin) used at the approved strength of 100 micrograms/gram (0.01%).

RhPDGF (recombinant human Platelet Derived Growth Factor-BB, Regranex™, becaplermin), an approved drug for treatment of chronic diabetic ulcers, was used as a positive control at the approved strength of 100 micrograms/gram (0.01%). At several time points, the wound area was traced onto clear plastic and was measured with an Image Analyzer. The incidence of animals reaching 75% wound closure was assessed and differences compared using Fisher's exact test. Differences were considered of statistical significance at p<0.05 levels.

Figure 3:
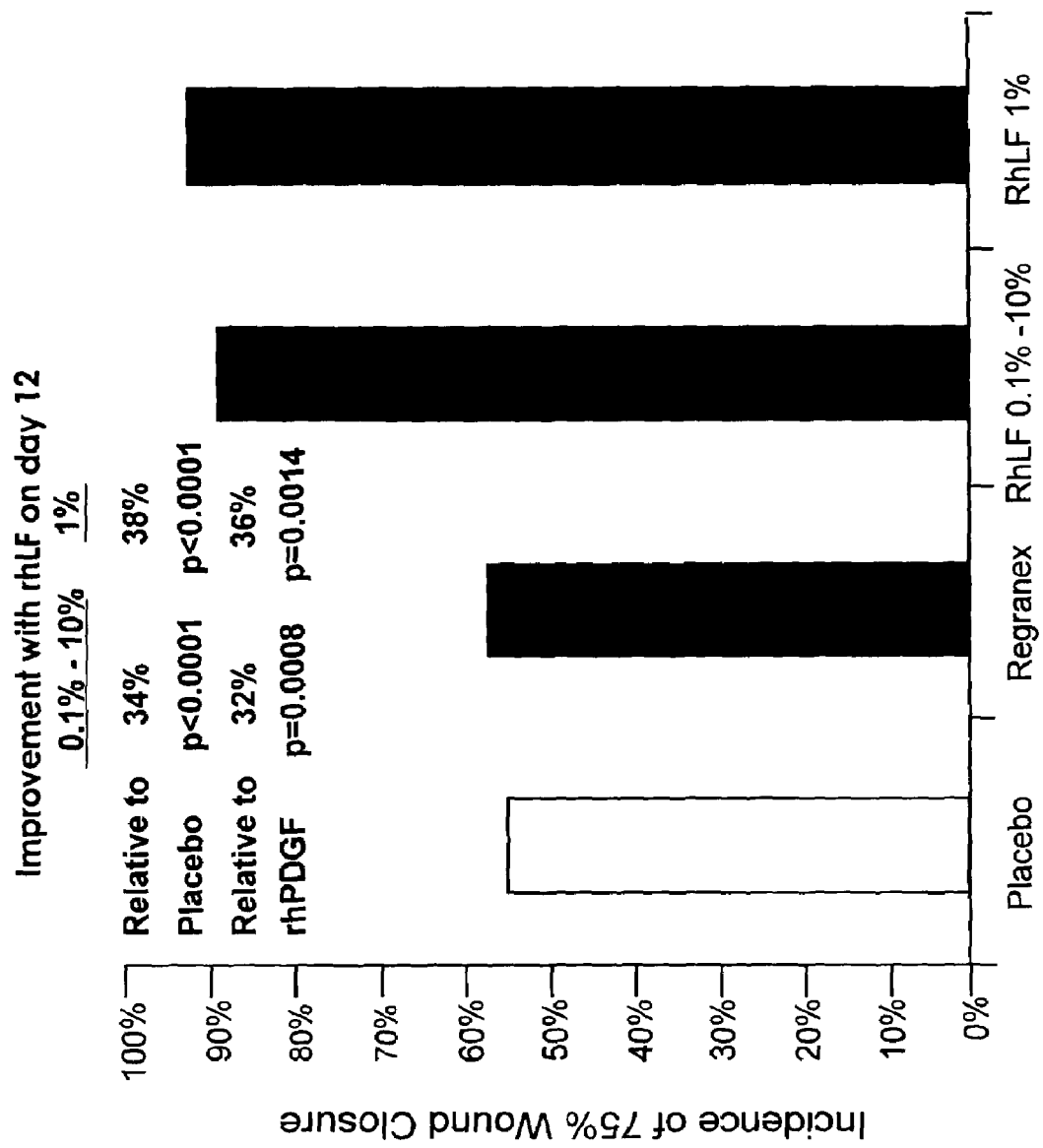
FIG. 3 shows the effect of topical rhLF on the incidence of 75% wound closure in healthy mice. Regranex™ was used as a positive control.

FIG. 3 shows pooled data from the 5 experiments, demonstrating the superior efficacy of rhLF compared to Regranex™ for wound repair at doses ranging from 0.1% to 10%. Animals treated with rhLF 0.1%-10% (147 animals) had a 34% increase in the incidence of 75% wound closure on the final day of the experiment relative to placebo (42 animals, p<0.0001) and a 32% increase relative to Regranex™ (21 animals, p<0.001). In healthy mice, 1% rhLF significantly (p<0.01) increased this parameter relative to placebo 38% and relative to becaplermin (Regranex™) 36% (p<0.01). In diabetic db/db mice with impaired wound repair function, 1% rhLF gel increased the incidence of 75% wound closure on day 15 by 83% over placebo (p<0.01).

Based on these results, it is envisioned that topical, oral, or parenteral lactoferrin results in the killing of bacteria infecting a wound, in the stimulation of IL-18, IL-12, GM-CSF, MIP-1α, MIP-1β, MIP-3α or IFN-γ, and in the inhibition of IL-2, IL-4, IL-5, IL-10, TNF-α, or matrix metalloproteinases. It is further envisioned that IL-18 or GM-CSF stimulate the production or activity of immune cells and cells involved in wound repair, and that TNF-alpha inhibits cells involved in inflammation.

Example 6

Efficacy of Oral rhLF in Wound Healing Experiments

Mice were anesthetized, the shoulder and back region of each animal was shaved, and a sharp punch (ID 12 mm) was used to remove the skin including *panniculus carnosus* and adherent tissues. Different doses of rhLF were applied topically to the wounds once per day for 11 days for normal mice or 20 days for diabetic db/db mice to compare the rates of healing with those of negative controls. Negative control or placebo was rhLF vehicle (a PBS solution). At several time points, the wound area was traced onto clear plastic and was measured with an Image Analyzer. The incidence of animals reaching 75% or 100% wound closure was assessed and differences compared using Fisher's exact test. Differences were considered of statistical significance at p<0.05 levels.

At several time points, the wound area was traced onto clear plastic and was measured with an Image Analyzer. The incidence of animals reaching 75% wound closure was assessed on days 9-12 for normal mice and days 15 or 19 for diabetic mice, and differences compared using Fisher's exact test. Differences were considered of statistical significance at p<0.05 levels.

FIG. 4A shows that oral rhLF given to healthy mice at doses ranging from 0.5 to 4.5 mg/Kg resulted in an improvement of 43% in the incidence of 75% wound closure compared to oral placebo, with the highest dose showing a 52% improvement (p<0.01). FIG. 4B shows that oral rhLF given to diabetic db/db mice at 4.5 to 65 mg/Kg doses of rhLF increased the incidence of 75% wound closure on day 15 by 75% over placebo with the highest dose tested achieving an increase of 83% over placebo (p<0.01). Similarly, FIG. 4C indicates that 4.5 to 65 mg/Kg doses of oral rhLF to diabetic db/db mice achieved 75% increase in incidence of 100% wound closure by day 19 with the highest dose reaching an increase of 100% compared to placebo (p<0.01).

Based on these results, it is envisioned that topical, oral, or parenteral lactoferrin results in the killing of bacteria infecting a wound, in the stimulation of IL-18, IL-12, GM-CSF, MIP-1α, MIP-1β, MIP-3α or IFN-γ, and in the inhibition of IL-2, IL-4, IL-5, IL-10, TNF-α, or matrix metalloproteinases. It is further envisioned that IL-18 or GM-CSF stimulate the production or activity of immune cells and cells involved in wound repair, and that TNF-alpha inhibits cells involved in inflammation.

Example 7

Topical and Oral rhLF Wound Healing Experiment in Infected Wounds

The efficacy of topical rhLF in bacteria-infected wounds was tested. This animal model represents a clinically relevant situation since diabetics often have infected ulcers and such infection is believed to contribute to the impairment of wound repair. *Staphylococcus aureus* is one of the most common bacteria infecting the diabetic foot ulcer and is associated with an increase in mortality rate.

Groups of 7 ICR male mice were anesthetized, the shoulder and back region of each animal was shaved, and a sharp punch (ID 12 mm) was used to remove the skin including *panniculus carnosus* and adherent tissues. Immediately after puncture, a $9.6 \times 10^5$ CFU/0.02 ml/mouse of *Staphylococcus aureus* (Smith) was applied to the wound region of each animal. The wound area, traced onto clear plastic sheets on days 3, 5, 7, 9 and 12, was quantitated with an Image Analyzer.

Topical rhLF, oral rhLF, vehicle (buffer), or a positive control (Regranex™ 0.01%) were applied immediately following injury and bacteria and once daily thereafter for a total of 11 consecutive days. For lactoferrin applied orally, mice were given 0.130 ml of the rhLF solution via gavage (directly feeding the animal with a flexible tube). The incidence of animals reaching 75% wound closure was assessed and differences compared using Fisher's exact test. Differences were considered of statistical significance at P<0.05 levels.

Figure 5B:
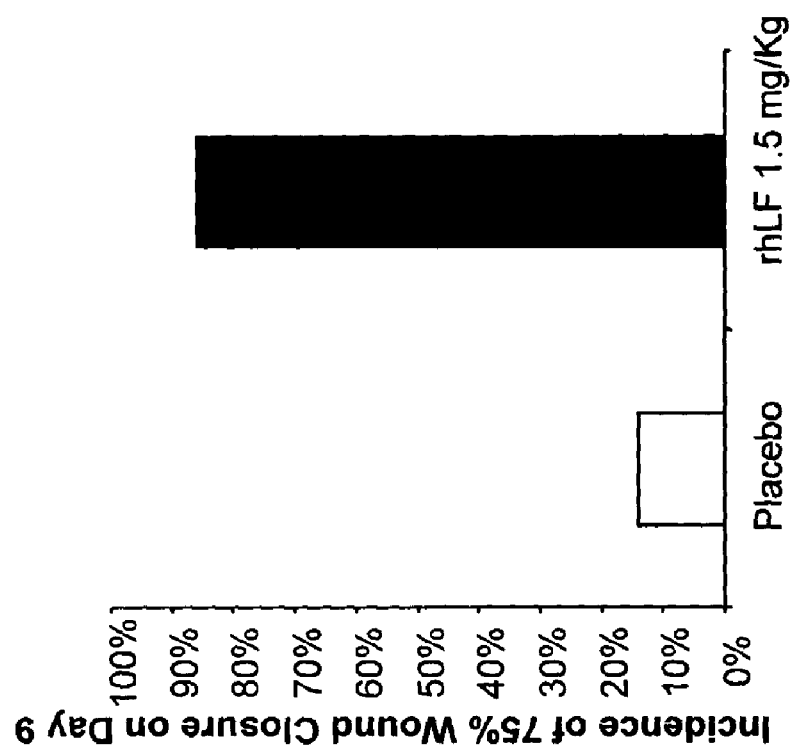
FIG. 5A and FIG. 5B show the incidence of 75% wound closure in an infected wound healed with and without topical (FIG. 5A) or oral (FIG. 5B) administration of recombinant human lactoferrin solution. Regranex™ was used as a topical positive control (FIG. 5A).
Figure 5A:
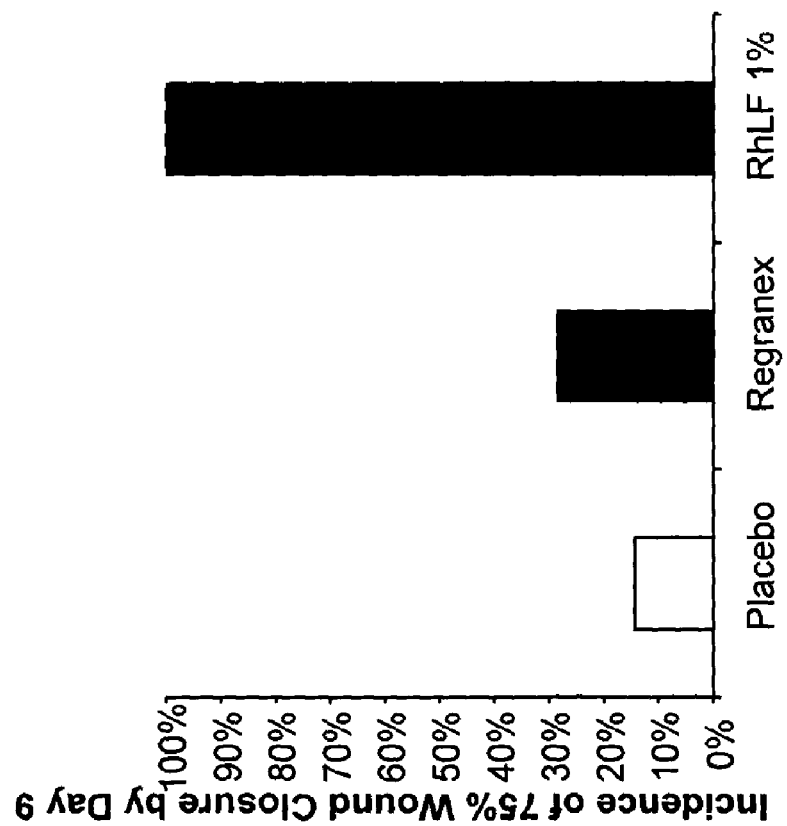

FIG. 5A and FIG. 5B shows that topical rhLF increased the incidence of 75% closure by 86% relative to placebo (p<0.01) and 71% relative to Regranex™ (p<0.05). FIG. 5B shows that oral rhLF improved the incidence of 75% closure by 72% relative to placebo (p<0.05).

Based on these results, it is envisioned that topical, oral, or parenteral lactoferrin results in the killing of bacteria infecting a wound, in the stimulation of IL-18, IL-12, GM-CSF, MIP-1α, MIP-1β, MIP-3α or IFN-γ, and in the inhibition of IL-2, IL-4, IL-S, IL-10, TNF-α, or matrix metalloproteinases. It is further envisioned that IL-18 or GM-CSF stimulate the production or activity of immune cells and cells involved in wound repair, and that TNF-alpha inhibits cells involved in inflammation.

Example 8

Best Topical rhLF Dose Determination

The experimental protocol in Example 5 is used to determine the lowest oral rhLF dose that promotes wound healing in mice. Smaller doses of rhLF are systematically tested until no further wound repair effect is apparent. EDTA is added in an attempt to increase the potency of rhLF and further decrease the rhLF dose that is effective. Topical vehicle is used as the negative control.

Example 9

Best Oral rhLF Dose Determination

The experimental protocol in Example 5 is used to determine the lowest oral rhLF dose that promotes wound healing in mice. Smaller doses of rhLF are systematically tested until no further wound repair effect is apparent. EDTA is added in an attempt to increase the potency of rhLF and further decrease the rhLF dose that is effective. Oral vehicle is used as the negative control.

Example 10

Combination Study

The experimental protocol in Example 5 is used to determine the rate of wound healing in mice. Combinations of oral with topical rhLF and oral rhLF with topical Regranex™ are tested with and without EDTA. Oral vehicle plus placebo gel, and oral vehicle plus Regranex™ are the negative and positive controls, respectively. Oral rhLF plus placebo gel, and oral vehicle plus topical rhLF are the synergy controls.

Example 11

Efficacy Comparison of RhLF Gel and Liquid Saline Formulations in Wounds Covered with Dressings The experimental protocol in Example 5 is used to determine the rate of wound healing in mice. Liquid formulations of rhLF, 0.2 mg/ml (0.02 ml of a 10 mg/ml solution) are applied to the wound. The wound area is then covered with a saline-moistened gauze dressing. This process is repeated daily for 10 days. RhLF Gel 0.2 mg [0.020 mL of a 10 mg/ml gel] is applied directly to the wounds and covered with a dressing, daily, for 10 days. 0.02 ml of rhLF solution vehicle and placebo gel are applied to wounds and covered with dressing, daily, for 10 days. Regranex™ is the positive control and is applied topically, 0.02 ml (100 µg/ml clinical concentration), in a similar fashion.

Example 12

Efficacy of Different Application Regimens of rhLF Gel and Dressings

The experimental protocol in Example 5 is used to determine the rate of wound healing in mice. RhLF Gel 0.2 mg [0.020 mL of a 10 mg/ml gel] is applied directly to the wounds and covered with a saline-moistened gauze dressing, daily, for 10 days. In another group of mice the dressing is changed every other day. In a third group, Regranex™: rhLF gel is applied to the wound and covered with a dressing. After 12 hours, the ulcer is rinsed gently with saline or water to remove residual gel, and the wound is covered with a fresh dressing for an additional 12 hours. Placebo gel 0.02 ml and Regranex™ 0.02 ml (100 µg/ml), are the negative and positive controls, respectively, and are applied using the latter regime.

Example 13

RhLF Gel: Comparison of Once Daily to Twice Daily

The experimental protocol in Example 5 is used to determine the rate of wound healing in mice. RhLF Gel 0.2 mg/wound/day [0.020 mL of a 10 mg/ml gel] is applied directly to the wounds, daily, for 10 days. To a second group of animals, 0.1 mg twice daily (BID) is applied, each application separated by a 12 hour interval. Placebo gel 0.02 ml and Regranex™, 0.02 ml (100 ug/ml), applied once per day, are the negative and positive controls, respectively.

Example 14

Efficacy of Topical rhLF Alone or in Combination with Regranex™

The experimental protocol in Example 5 is used to determine the rate of wound healing in mice. RhLF Gel 0.2 mg/wound/day [0.020 mL of a 10 mg/ml gel] is applied directly to the wounds daily, for 10 days. A second group of mice receives rhLF 0.2 mg/wound and Regranex™ 2 ug/wound (0.02 ml/wound, 100 ug/ml). A third group gets rhLF 0.02 mg/wound and Regranex™ 0.002 ug/wound to test for potential synergies. Placebo gel 0.02 ml, placebo plus Regranex™ 0.02 ml (100 ug/ml), and Regranex™ alone, are the negative, synergy, and positive controls, respectively.

Example 15

Dose Escalation, Pharmacokinetic and Pharmacodynamic Trial of Topical rhLF in Patients with Diabetic Ulcers This is a Phase I/II 14-day dose escalation study in humans designed to evaluate the escalating dosing regimens of topical rhLF gel in patients with chronic diabetic ulcers and determine a maximally tolerated dose (if any) for 1% up to 8.5% rhLF concentration. RhLF is evaluated for its ability to promote ulcer healing.

Example 16

Dose Escalation, Pharmacokinetic and Pharmacodynamic Trial of Oral rhLF in Patients with Diabetic Ulcers Study design is similar to the one in Example 14, except that the rhLF is applied orally with and without EDTA.

Example 17

Trial of rhLF versus placebo and Standard-of-Care in Patients with Diabetic Ulcers This is a randomized, double-blind, placebo-controlled, multicenter study in humans. It is a 12-week phase II clinical trial in patients with diabetic chronic ulcers to evaluate the efficacy of treatment with two dose levels of a topical or oral administration of rhLF in comparison with placebo, Regranex™, and standard-of care only. Efficacy is evaluated by incidence of partial and complete wound closure, and time to healing.

Example 18

Release of rhLF from the Carbomer Gels

RhLF-Carbopol-980 gels at several concentration strengths are tested for release kinetics of rhLF over time from the dosage form and are detected in a receiving buffer in an in vitro diffusion system.

Example 19

Additional Studies of rhLF-Vinyl Polymer Gels

RhLF containing gels are prepared based on polymethacrylic acid, polyvinyl pyrrolidone and polyvinyl alcohol polymers. Viscosity of gels is determined via a Brookfield DV-III+Rheometer and protein content uniformity is measured using the BCA assay, as described in example 1. Bioavailability is assessed following application of these vinyl polymer gels on open, full-thickness wounds in normal mice, as described in example 2. Efficacy of wound healing activity of these vinyl polymer gel formulations is tested in mouse model as described in examples 3-5. Several concentration strengths of these vinyl polymer gels are tested for release kinetics of rhLF over time from the dosage form and are detected in a receiving buffer in an in vitro diffusion system.

Example 20

Studies of rhLF-Polysaccharide Polymer Gels

RhLF-Polysaccharide polymer gel formulations are prepared. Viscosity of gels is determined via a Brookfield DV-III+Rheometer and protein content uniformity is measured using the BCA assay, as described in example 1. Bioavailability is assessed following application of the polysaccharide polymer gels on open, full-thickness wounds in normal mice, as described in example 2. Efficacy of wound healing activity of the polysaccharide polymer gel formulations is tested in mouse model as described in examples 3-5. Several concentration strengths of the polysaccharide polymer gels are tested for release kinetics of rhLF over time from the dosage form and are detected in a receiving buffer in an in vitro diffusion system.

Example 21

Studies of rhLF-Glycosaminoglycan Polymer Gels

RhLF-Glycosaminoglycan polymer gel formulations are prepared. Viscosity of gels is determined via a Brookfield DV-III+ Rheometer and protein content uniformity is measured using the BCA assay, as described in example 1. Bioavailability is assessed following application of these glycosaminoglycan polymer gels on open, full-thickness wounds in normal mice, as described in example 2. Efficacy of wound healing activity of the glycosaminoglycan polymer gel formulations is tested in mouse model as described in examples 3-5. Several concentration strengths of the glycosaminoglycan polymer gels are tested for release kinetics of rhLF over time from the dosage form and are detected in a receiving buffer in an in vitro diffusion system.

Example 22

Studies of rhLF-Protein Polymer Gels

RhLF-Protein polymer gel formulations are prepared. Viscosity of gels is determined via a Brookfield DV-III+Rheometer and protein content uniformity is measured using the BCA assay, as described in example 1. Bioavailability is assessed following application of these protein polymer gels on open, full-thickness wounds in normal mice, as described in example 2. Efficacy of wound healing activity of the protein polymer gel formulations is tested in mouse model as described in examples 3-5. Several concentration strengths of the protein polymer gels are tested for release kinetics of rhLF over time from the dosage form and are detected in a receiving buffer in an in vitro diffusion system.

Example 23

Studies of rhLF-Pluronic Polymer Gels

RhLF-Pluronic polymer gel formulations are prepared. Viscosity of gels is determined via a Brookfield DV-III+ Rheometer and protein content uniformity is measured using the BCA assay, as described in example 1. Bioavailability is assessed following application of these pluronic polymer gels on open, full-thickness wounds in normal mice, as described in example 2. Efficacy of wound healing activity of the pluronic polymer gel formulations is tested in mouse model as described in examples 3-5. Several concentration strengths of the pluronic polymer gels are tested for release kinetics of rhLF over time from the dosage form and are detected in a receiving buffer in an in vitro diffusion system.

Example 24

Studies of rhLF-Acrylamide Polymer Gels

RhLF-Acrylamide polymer gel formulations are prepared. Viscosity of gels is determined via a Brookfield DV-III+ Rheometer and protein content uniformity is measured using the BCA assay, as described in example 1. Bioavailability is assessed following application of these acrylamide polymer gels on open, full-thickness wounds in normal mice, as described in example 2. Efficacy of wound healing activity of the acrylamide polymer gel formulations is tested in mouse model as described in examples 3-5. Several concentration strengths of the acrylamide polymer gels are tested for release kinetics of rhLF over time from the dosage form and are detected in a receiving buffer in an in vitro diffusion system.

Example 25

Wound Healing Rates with RhLF Preparations Differing in Proportion of N−1 Truncate The biological activity of preparations of rhLF differing in the percentage of N−1 truncates was compared using a mouse model of wound healing. Groups of seven mice were anesthetized, the shoulder and back region of each animal was shaved, and a sharp punch (ID 12 mm) was used to remove the skin including *panniculus carnosus* and adherent tissues (open, full-thickness wounds). Either rhLF (20 microgram per mouse) or placebo was applied topically to the wounds once per day for 11 days. At several time points, the wound area was traced onto clear plastic and was measured with an Image Analyzer. The CT50 (time to 50% closure) was assessed. (Experiments AN-W2, W3, W9).

As shown in Table 7, rhLF preparations containing entirely intact protein as well as those containing N−1 truncates ranging from 27% to 42% all showed efficacy relative to their respective placebos that was statistically significant. Percent improvement between the batches was comparable and statistically indistinguishable.

TABLE 7

| Wound Healing Rates With Three Different RhLF Preparations | | | |
|---|---|---|---|
| RhLF Preparation | CT50 (Active/Placebo) | Percent Improvement | Percent N-1 Truncate |
| 7001 | 4.8/5.9 Days | 19% | 0% |
| L005 | 6.0/7.6 Days | 21% | 27% |
| L007 | 5.3/6.4 Days | 17% | 42% |

Example 26

Wound Closure Incidence with RhLF Preparations Differing in Proportion of N−1 Truncate In the experiments described in Example 25, incidence of 80% wound closure was measured in mice treated with placebo or rhLF. The absolute increase in the incidence of 80% wound closure in rhLF treated animals relative to placebo animals in the same experiment was determined on Day 9 (7001 and L007) or Day 12 (L005).

As shown in Table 8, rhLF preparations containing entirely intact protein as well as those containing N-1 truncates ranging from 27% to 42% all showed efficacy with an increased wound closure that was statistically significant with respect to their respective placebos.

TABLE 8

Wound Closure Incidence With Three Different RhLF Preparations

| RhLF Preparation | 80% Closure (Active/Placebo) | Percent Improvement | Percent N-1 Truncate |
|---|---|---|---|
| 7001 | 86%/57% | 29% | 0% |
| L005 | 43%/0% | 43% | 27% |
| L007 | 43%/0% | 43% | 42% |

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 4,554,101
U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,571,691
U.S. Pat. No. 5,571,697
U.S. Pat. No. 5,571,896
U.S. Pat. No. 5,629,001
U.S. Pat. No. 5,635,377
U.S. Pat. No. 5,789,166
U.S. Pat. No. 5,919,913
U.S. Pat. No. 6,066,469
U.S. Pat. No. 6,080,559
U.S. Pat. No. 6,100,054
U.S. Pat. No. 6,277,817
U.S. Pat. No. 6,228,614
U.S. Pat. No. 6,333,311
U.S. Pat. No. 6,455,687
Edmonds M, et al., *Diabetes Metab Res Rev.* 2000; 16 (Suppl 1): S51-S54.
Kuhara T, et al., *Nutr Cancer.* 2000, 38(2):192-9.
Lipsky B A and Berendt R A, *Diabetes Metab Res Rev.* 2000; 16(Suppl 1): S42-S46.
Mandracchia V J, et al., *Clin Pod Med Surg.* 2001; 18: 189-209.
Montesinos M C, et al., *J Exp Med.* 1997; 186:1615-1620.
Moulin V, et al., *Cell Mol. Biol.* 1998; 44: 961-971.
Weiman J T. *Am J Surg.* 1998; 176 (Suppl 2A): 74S-79S.
Victor-Vega C, et al., *Inflammation.* 2002; 26: 19-24.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating a skin wound, the method comprising the step of administering a therapeutically effective amount of a lactoferrin composition to a subject having the skin wound to result in an improvement or a remediation of a symptom of the skin wound and wherein the skin wound is selected from the group consisting of a venous stasis ulcer, a pressure ulcer and a diabetic ulcer.

2. The method of claim 1, wherein said lactoferrin composition is administered topically, orally or parenterally.

3. The method of claim 2, wherein said lactoferrin composition is administered orally.

4. The method of claim 3 further comprising administering an antacid in conjunction with said lactoferrin composition.

5. The method of claim 2, wherein said lactoferrin composition is administered topically.

6. The method of claim 2, wherein said lactoferrin composition is administered parenterally.

7. The method of claim 1 further comprising administering a standard wound healing therapy in combination with the lactoferrin composition.

8. The method of claim 1, wherein the administering comprises administering said composition for at least one week to twelve weeks.

9. The method of claim 1, wherein the amount of the lactoferrin that is administered is about 0.0001 microgram to about 100 g per day.

10. The method of claim 1, wherein said composition is a topical gel, a solution, capsule or a tablet having a lactoferrin concentration of about 0.0001% to about 30%.

11. The method of claim 10, wherein said topical gel is composed from a polymer selected from the group of consisting of a vinyl polymer, polysaccharide polymer, glycosaminoglycan polymer, protein polymer, polyoxyethylene-polyoxypropylene polymer, carbomers and acrylamide polymer.

12. The method of claim 11, wherein the polymer concentration is about 0.5% (w/w) to about 3.0% (w/w) and the polymer has a molecular weight of about 50,000 to about 13,000,000.

13. A method of treating a skin wound, the method comprising the step of administering a therapeutically effective amount of a lactoferrin composition to a subject having the skin wound to result in an improvement or a remediation of a symptom of the skin wound, wherein said lactoferrin composition is administered orally or parenterally and wherein the skin wound is selected from the group consisting of a laceration, a penetrating wound, a *Staphylococcus aureus* infected wound, a venous stasis ulcer, a pressure ulcer, a surgical wound and an open full-thickness skin puncture wound.

14. The method of claim 13, wherein said lactoferrin composition is administered orally.

15. The method of claim 14 further comprising administering an antacid in conjunction with said lactoferrin composition.

16. The method of claim 13 further comprising administering a standard wound healing therapy in combination with the lactoferrin composition.

17. The method of claim 13, wherein the administering comprises administering said composition for at least one week to twelve weeks.

18. The method of claim 13, wherein the amount of the lactoferrin that is administered is about 0.0001 microgram to about 100 g per day.

* * * * *